US009039414B2

(12) United States Patent
Bulloch et al.

(10) Patent No.: US 9,039,414 B2
(45) Date of Patent: May 26, 2015

(54) DRILL GUIDE PIN, SHANK, CANNULATED DRILL BIT, AND DRIVER FOR CREATING A HOLE IN A BONE

(76) Inventors: Scott E. Bulloch, St. George, UT (US); Russell G. Olsen, Cedar City, UT (US)

( * ) Notice: Subject to any disclaimer, the term of this patent is extended or adjusted under 35 U.S.C. 154(b) by 117 days.

(21) Appl. No.: 13/019,161

(22) Filed: Feb. 1, 2011

(65) Prior Publication Data

US 2011/0123946 A1    May 26, 2011

Related U.S. Application Data

(63) Continuation-in-part of application No. 12/367,381, filed on Feb. 6, 2009, now abandoned.

(51) Int. Cl.
*A61C 3/00* (2006.01)
*A61C 1/08* (2006.01)
*A61C 8/00* (2006.01)

(52) U.S. Cl.
CPC ............... *A61C 1/084* (2013.01); *A61C 8/0089* (2013.01)

(58) Field of Classification Search
CPC .......... A61C 1/082; A61C 1/084; A61C 1/14; A61C 3/02; A61C 3/06; A61C 5/025; A61C 8/0089; A61C 19/04; A61B 17/0401; A61B 17/15; A61B 17/1615; A61B 17/1617; A61B 17/1633; A61B 17/1637; A61B 17/17; A61B 17/1739; A61B 17/32002; A61B 17/7082; A61B 17/864; A61B 2017/0409; A61B 2019/462
USPC ........... 433/72, 75, 165, 51, 74, 76, 114, 122, 433/123, 125, 126, 142, 166, 215; 606/96, 606/80, 97, 98, 104, 304, 323; 408/214, 408/241 G
See application file for complete search history.

(56) References Cited

U.S. PATENT DOCUMENTS

| 1,910,592 A | 5/1933 | Craigo |
| 2,608,762 A | 9/1952 | Fox |
| 3,276,122 A | 10/1966 | Slayton |

(Continued)

FOREIGN PATENT DOCUMENTS

WO    2010-090665 A1    8/2010

OTHER PUBLICATIONS

Office Action for U.S. Appl. No. 12/367,381 dated Jul. 13, 2011.
(Continued)

*Primary Examiner* — Cris L Rodriguez
*Assistant Examiner* — Justin O'Donnell
(74) *Attorney, Agent, or Firm* — Kunzler Law Group, PC

(57) ABSTRACT

According to one embodiment, a dental implant system for implanting a dental implant in bone tissue using an implant drill driver includes a shank and a drill guide. The shank is removably coupleable to the implant drill driver and includes an internal passage that has a non-round cross-sectional shape. When coupled to the implant drill driver, the shank is rotatable via operation of the implant drill driver. The drill guide pin includes a bone penetrating end portion and a shank engagement portion. The shank engagement portion includes a notched section having a non-round cross-sectional shape corresponding with the non-round cross-sectional shape of the internal passage of the shank. The notched section of the shank engagement portion is insertable within the internal passage of the shank. Moreover, engagement between the notched section and the internal passage facilitates co-rotation of the shank and drill guide pin.

13 Claims, 12 Drawing Sheets

(56) References Cited

U.S. PATENT DOCUMENTS

| | | | |
|---|---|---|---|
| 3,375,584 A | | 4/1968 | Morris |
| 3,895,444 A | | 7/1975 | Small |
| 4,450,835 A | * | 5/1984 | Asnis et al. ............... 606/96 |
| 4,478,580 A | | 10/1984 | Barrut |
| 4,624,639 A | | 11/1986 | Wong |
| 4,710,075 A | | 12/1987 | Davison |
| 4,872,451 A | | 10/1989 | Moore et al. |
| 5,163,842 A | | 11/1992 | Nonomura |
| 5,221,204 A | | 6/1993 | Kruger et al. |
| 5,320,529 A | | 6/1994 | Pompa |
| 5,341,459 A | | 8/1994 | Backes |
| 5,374,270 A | * | 12/1994 | McGuire et al. ............ 606/80 |
| 5,445,639 A | * | 8/1995 | Kuslich et al. ............. 606/80 |
| 5,452,219 A | | 9/1995 | Dehoff et al. |
| 5,604,677 A | | 2/1997 | Brien |
| 5,613,852 A | | 3/1997 | Bavitz |
| 5,718,579 A | | 2/1998 | Kennedy |
| 5,741,267 A | | 4/1998 | Jorneus et al. |
| 5,743,916 A | | 4/1998 | Greenberg et al. |
| 5,785,522 A | | 7/1998 | Bergstrom et al. |
| 5,915,962 A | | 6/1999 | Rosenlicht |
| 5,967,777 A | | 10/1999 | Klein et al. |
| 6,030,211 A | | 2/2000 | Sandhaus |
| 6,073,058 A | | 6/2000 | Cossen et al. |
| 6,123,546 A | | 9/2000 | Bergstrom et al. |
| 6,250,919 B1 | | 6/2001 | Haje |
| 6,296,483 B1 | | 10/2001 | Champleboux |
| 6,382,975 B1 | | 5/2002 | Poirier |
| 6,499,221 B1 | * | 12/2002 | Kuhn et al. ............... 33/514 |
| 6,695,841 B2 | | 2/2004 | Feiler et al. |
| 6,739,872 B1 | | 5/2004 | Turri |
| 6,785,572 B2 | | 8/2004 | Yanof et al. |
| 6,793,491 B2 | | 9/2004 | Klein et al. |
| 6,804,581 B2 | | 10/2004 | Wang et al. |
| 6,869,282 B2 | | 3/2005 | Carmichael et al. |
| 6,913,463 B2 | | 7/2005 | Blacklock |
| 7,044,735 B2 | | 5/2006 | Malin |
| 7,086,860 B2 | | 8/2006 | Schuman et al. |
| 7,097,451 B2 | | 8/2006 | Tang |
| 7,322,821 B1 | | 1/2008 | Lin |
| 7,331,786 B2 | | 2/2008 | Poirier |
| 2001/0018583 A1 | * | 8/2001 | Bays ........................... 604/516 |
| 2001/0044094 A1 | | 11/2001 | Schostek et al. |
| 2001/0053510 A1 | | 12/2001 | Ranalli |
| 2002/0086263 A1 | | 7/2002 | Kyung |
| 2002/0102517 A1 | | 8/2002 | Poirier |
| 2002/0137002 A1 | | 9/2002 | Bodenmiller |
| 2004/0048225 A1 | | 3/2004 | Fletcher |
| 2004/0219479 A1 | | 11/2004 | Malin et al. |
| 2004/0259051 A1 | | 12/2004 | Brajnovic |
| 2005/0003327 A1 | | 1/2005 | Elian et al. |
| 2005/0170311 A1 | | 8/2005 | Tardieu et al. |
| 2005/0261698 A1 | * | 11/2005 | Powell ........................ 606/96 |
| 2005/0273107 A1 | * | 12/2005 | Stevens ...................... 606/73 |
| 2005/0287492 A1 | | 12/2005 | Lazzarato |
| 2006/0093988 A1 | | 5/2006 | Swaelens et al. |
| 2006/0210949 A1 | | 9/2006 | Stoop |
| 2006/0240378 A1 | | 10/2006 | Weinstein et al. |
| 2006/0257817 A1 | | 11/2006 | Shelton |
| 2006/0281046 A1 | | 12/2006 | Heo |
| 2007/0077532 A1 | | 4/2007 | Harter |
| 2007/0099150 A1 | * | 5/2007 | Muller et al. ............. 433/165 |
| 2007/0156241 A1 | | 7/2007 | Reiley et al. |
| 2007/0190492 A1 | | 8/2007 | Schmitt |
| 2007/0212666 A1 | | 9/2007 | Poirier |
| 2007/0239159 A1 | | 10/2007 | Altarac et al. |
| 2008/0064005 A1 | | 3/2008 | Meitner |
| 2008/0085489 A1 | | 4/2008 | Schmitt |
| 2008/0154304 A1 | | 6/2008 | Crawford et al. |
| 2008/0228303 A1 | | 9/2008 | Schmitt |
| 2010/0233647 A1 | | 9/2010 | Yang |

OTHER PUBLICATIONS

Final Office Action for U.S. Appl. No. 12/367,381 dated Jul. 12, 2012.

PCT/US2012/023532 International Search Report and Written Opinion mailed Aug. 22, 2012.

PCT/US2009/064042 International Search Report and Written Opinion mailed Jun. 9, 2010.

* cited by examiner

DRILL GUIDE PIN, SHANK, CANNULATED DRILL BIT, AND DRIVER FOR CREATING A HOLE IN A BONE

CROSS-REFERENCE TO RELATED APPLICATION

This application is a continuation-in-part of U.S. patent application Ser. No. 12/367,381, filed Feb. 6, 2009 now abandoned, which is incorporated herein by reference.

FIELD

This invention relates to dental implants and more particularly to a dental implant system for placing and installing dental implants.

BACKGROUND

Practitioners, such as dentists or oral surgeons, use various techniques and devices for placing and installing dental implants or other prosthetics in a patient's mouth. Generally, dental implants are placed and installed using non-cannulated drilling techniques for drilling a hole into the jaw bone of the patient and securely positioning the dental implant within the formed hole. The size, shape, and orientation of the formed holes are important because the holes typically dictate the fit and orientation of the dental implant.

Conventional hole forming techniques in dental applications include accessing the portion of the jawbone where the dental implant will be placed by creating incisions in the patient's gums. The practitioner then pushes each flap of gum tissue back to expose the underlying bone. Generally, once the bone is exposed, the practitioner uses a series of incrementally larger diameter drill bits (also commonly referred to as "drills") to prepare the hole into which the implant is placed. More specifically, according to several known techniques, a drill guide splint is formed from a cast of the patient's mouth and placed in the patient's mouth. The drill guide splint is used to direct round burs and/or bone drill bits in place during drilling. A small round bur or drill bit is first used to form a divot in the bone. A pilot drill bit is then used to form a pilot hole in the bone for positioning larger drill bits.

After the pilot hole is formed, the practitioner evaluates the positioning, orientation and angle of the implant hole by inserting an alignment pin into the implant hole. If the alignment is correct, the practitioner uses the pilot drill bit to drill the total depth needed for the implant. The practitioner incrementally expands the hole to a final size by utilizing several drill bits of increasing diameter. The dental implant is then placed in and secured to the formed hole.

In contrast to dental applications, the use of cannulated drill systems for forming holes in non-dental human tissue is known in the art. Although some cannulated drill systems have been used to form holes in human tissue, such systems are not adapted for use in dental applications.

SUMMARY

The subject matter of the present application has been developed in response to the present state of the art, and in particular, in response to the problems and needs in the art that have not yet been fully solved by currently available dental implant placement and installation techniques. Accordingly, the subject matter of the present application has been developed to provide a dental implant system and associated methods that overcomes at least some of the shortcomings of the prior art.

There are several shortcomings associated with currently available dental implant placement and installation systems. First, accurate placement and orientation of the round bur and pilot drill bit on the patient's bone can be difficult. Not only must the pilot hole be oriented in a correct position, but it must also be oriented at a correct angle. Currently available systems do not provide for consistent placement and orientation of dental implant holes.

Second, once a pilot hole has been formed, relocating the hole is very difficult. Accordingly, if the divot or pilot hole is initially formed in the wrong position, a new divot and pilot hole must be drilled and the old hole is wasted. Further, due to the size of the pilot drill bit, significant damage to the bone and overlying soft tissue may occur, which can make repositioning of a new hole difficult.

Third, with conventional systems, there is a risk that the drill will contact the guide splint as the drills cuts. If the drill contacts the guide splint, pieces of the guide splint may be removed from the guide splint and become lodged in the surgical site.

Finally, after the pilot drill bit is removed, conventional systems do not include a mechanism for directionally guiding the subsequent larger drill bits. Directional guidance is provided only by positioning the larger drill bits over the previously drilled hole. The larger drill bits often vary from the orientation of the previously drilled path. This can be problematic for dental applications where bone angles or slopes necessitate accurately positioned and oriented holes as only slight variances can severely damage the patient's bone.

Described herein are several embodiments of a dental implant drilling system that overcomes one or more of the shortcomings of prior art systems. For example, in some implementations, the dental implant system provides improved directional guidance and low impact drilling such that the initial positioning of the hole can be redone if necessary. Further, in some implementations, the dental implant system promotes improved transfer of information obtained in laboratory settings to actual surgery to facilitate more accurate drilling techniques. Some dental implant systems described herein reduce the risk of fragments being removed from the guide splint and contaminating the surgical site. Further, in some embodiments, the speed of implanting and accuracy of the implants can be improved. Additionally, various embodiments of the dental implant systems described herein provide directional information and guidance after the pilot hole is formed by the pilot drill bit.

According to one embodiment, a cannulated dental implant system for implanting a dental implant in bone tissue includes a guide splint having at least one guide sleeve defining a guide channel. The system also includes a guide pin with a bone penetrating end portion. The guide pin is extendable through the guide channel and drivable into bone tissue. In some implementations, the guide pin includes a series of markings indicating a depth of the guide pin in the bone tissue. Further, the system includes a first drill bit with a first outer diameter and an axial channel sized to receive the guide pin. The first drill bit is rotatable about the guide pin to drill a hole into the bone tissue. The hole has a diameter corresponding with the first outer diameter. The system includes a second drill bit with a second outer diameter that is greater than the first outer diameter. The second drill bit further includes an axial channel sized to receive the guide pin. Moreover, the second drill bit is rotatable about the guide pin to enlarge the hole in the bone tissue to correspond with the second outer diameter. Additionally, the system includes a dental implant securable within the enlarged hole.

In some implementations, the guide splint includes a plurality of guide sleeves. At least two of the plurality of guide sleeves can be oriented at different angles with respect to each other. In certain implementations, the at least one guide sleeve is removably secured to the guide splint. The at least one guide sleeve can be positioned within a hole formed in the guide splint.

According to yet some implementations, the guide splint can include at least two separable interconnected portions. The at least two separable interconnected portions are separable along a cut coextensive with a line extending through at least one of the guide sleeves. The two separable interconnected portions can include at least first and second portions. The first portion can include at least one first engagement element and the second portion can include at least one second engagement element corresponding with the first engagement element. The first and second engagement elements can be engageable to couple the first and second portions together and disengageable to separate the first and second portions from each other. The first engagement element can include an at least partially circular element and the second engagement element comprises an at least partially flexible socket configured to removably retain the at least partially circular element.

In some implementations, the system further includes a drilling assembly that includes a guide splint orientation adjustment stand removably coupled to a drill press. The drill press can include a first mating feature. The guide splint orientation adjustment stand can include a second mating feature matingly engageable with the first mating feature to removably secure the guide splint orientation adjustment stand in a desired position relative to the drill press. The guide splint orientation adjustment stand can be pivotable to orient a guide splint secured to the orientation adjustment stand in any of an infinite number of 3-dimensional orientations.

According to another embodiment, a method for implanting dental implants in bone tissue includes making a dental splint that includes at least one sleeve at a location corresponding with a desired implant location and positioning the dental splint over a set of teeth. The method further includes driving a guide pin through the at least one sleeve and into bone tissue and removing the dental splint from the set of teeth. Additionally, the method includes engaging a first drill bit with the guide pin and drilling a hole in the bone tissue with the first drill bit while engaged with the guide pin, as well as engaging a second drill bit with the guide pin and expanding the hole in the bone tissue with the second drill bit while engaged with the guide pin. The method also includes removing the guide pin from the bone tissue and positioning a dental implant in the expanded hole in the bone tissue.

In some implementations of the method, removing the dental splint from the set of teeth includes separating the dental splint into at least two pieces and individually removing the two pieces from the set of teeth. Separating the dental splint into at least two pieces can include disengaging corresponding engagement elements each coupled to a respective one of the two pieces.

According to yet some implementations, removing the dental splint from the set of teeth includes removing the at least one sleeve from the guide splint then removing the dental splint without the at least one sleeve from the set of teeth. In yet certain implementations, making the dental splint includes drilling a hole in the splint and positioning the at least one sleeve in the splint hole.

In some implementations, the method includes making a cast of the set of teeth, drilling at least one hole in the cast at the location corresponding with the desired implant location, positioning a radiopaque marker in the at least one hole, and forming the dental splint over the cast and radiopaque marker where the radiopaque marker is secured within the dental splint. The method can also include placing the dental splint with radiopaque marker over the set of teeth and imaging the dental splint and set of teeth and comparing the location and orientation of the radiopaque marker with a desired location and orientation of the dental implant. The method can include drilling a hole in the splint based on the comparison between the location and orientation of the radiopaque marker and the desired location and orientation of the dental implant. The dental splint can include a plurality of sleeves and driving a guide pin can include driving a plurality of drive pins through respective sleeves of the plurality of sleeves.

In another embodiment, a dental implant system for implanting a dental implant in bone tissue includes a plurality of guide sleeves each defining a differently sized guide channel, a guide splint positionable over a set of teeth where the guide splint includes a hole configured to individually receive each of the plurality of guide sleeves, and a plurality of drill bits each differently sized to correspond with a respective one of the differently sized guide channels of the plurality of guide sleeves. Each of the plurality of drill bits is configured to extend through the corresponding respective guide channel to form a hole in bone tissue.

According to yet another embodiment, a method for implanting dental implants in bone tissue includes making a dental splint comprising a hole at a location corresponding with a desired implant location and in an orientation corresponding with a desired implant orientation. The hole is formed using a medical imaging process. The method further includes positioning the dental splint over a set of teeth. Also, the method includes inserting a first guide sleeve defining a first guide channel having a first dimension into the dental splint hole. Additionally, the method includes extending a first drill bit having a first outer diameter corresponding with the first dimension through the first guide channel of the first guide sleeve and drilling a first hole in the bone tissue. The first hole has a size corresponding with the first outer diameter. Further, the method includes removing the first guide sleeve from the dental splint hole and inserting a second guide sleeve defining a second guide channel having a second dimension into the dental splint hole. The second dimension is larger than the first dimension. The method also includes extending a second drill bit having a second outer diameter corresponding with the second dimension through the second guide channel of the second guide sleeve and drilling a second hole in the bone tissue in place of the first hole. The second hole has a size corresponding with the second outer diameter. The method further includes removing the dental splint from the set of teeth and positioning a dental implant in the second hole.

According to yet another embodiment, a dental implant system for implanting a dental implant in bone tissue using an implant drill driver includes a shank and a drill guide. The shank is removably coupleable to the implant drill driver and includes an internal passage that has a non-round cross-sectional shape. When coupled to the implant drill driver, the shank is rotatable via operation of the implant drill driver. The drill guide pin includes a bone penetrating end portion and a shank engagement portion. The shank engagement portion includes a notched section having a non-round cross-sectional shape corresponding with the non-round cross-sectional shape of the internal passage of the shank. The notched section of the shank engagement portion is insertable within the internal passage of the shank. Moreover, engagement between the notched section and the internal passage facilitates co-rotation of the shank and drill guide pin.

In some implementations of the dental implant system, the non-round cross-sectional shape of the internal passage and the notched section of the shank engagement portion is a generally D-shape. The dental implant system can also include a cannulated drill bit. The drill guide pin is configured to receive thereabout the cannulated drill bit and the cannulated drill bit is removably coupleable to the implant drill driver. The shank can include a first driver coupling feature and the cannulated drill bit can include a second driver coupling feature. The first and second driver coupling features can be identical.

According to certain implementations of the dental implant system, the notched section of the shank engagement portion extends lengthwise along only a portion of the drill guide pin. The internal passage can extend axially through the shank from a first end of the shank to a second end of the shank. In certain implementations, a cross-sectional size of the notched section of the shank engagement portion is slightly smaller than a cross-sectional size of the internal passage of the shank.

According to anther embodiment, a guide pin for receiving and positioning a cannulated drill bit in a bone drilling procedure includes a bone penetrating end portion, a notched section having a non-circular cross-sectional shape, and an elongate shaft extending between the bone penetrating end portion and the notched section. The shaft has a circular cross-sectional shape.

According to some implementations, the non-circular cross-sectional shape is a D-shape. The elongate shaft can include a series of markings indicating a depth of the guide pin in bone tissue. In certain implementations, the notched section has a cross-sectional area that is smaller than a cross-sectional area of the elongate shaft. The outer surface of the elongate shaft can be substantially smooth and the bone penetrating end portion can have a pointed tip. In some implementations, an intersection of the notched section and elongate shaft includes a stop. Also, the guide pin can be fluteless, as opposed to typical drill bits, which include one or more spiraling flutes adjacent spiraling cutting blades.

In another embodiment, a method for drilling bone tissue includes removably coupling a shank to a bone drill driver where the shank includes an internal passage that has a non-round cross-sectional shape. The method also includes inserting a shank engagement portion of a guide pin into the internal passage of the shank. The shank engagement portion includes a keyed-in section having a non-round cross-sectional shape matching the non-round cross-sectional shape of the internal passage of the shank. Additionally, the method includes co-rotating the shank and the guide pin via actuation of the bone drill driver and engagement between the shank engagement portion of the guide pin and the internal passage of the shank. The method further includes driving the rotating guide pin into bone tissue.

In certain implementations, the method includes removing the shank engagement portion of the guide pin driven into bone tissue from the internal passage of the shank. The method may also include decoupling the shank from the bone drill driver and removably coupling a cannulated drill bit to the bone drill driver. Further, the method may include positioning the driven guide pin through the cannulated drill bit and rotating the cannulated drill bit via actuation of the bone drill driver. The method can include driving the rotating cannulated drill bit into bone tissue surrounding the driven guide pin.

Reference throughout this specification to features, advantages, or similar language does not imply that all of the features and advantages that may be realized with the subject matter of the present disclosure should be or are in any single embodiment. Rather, language referring to the features and advantages is understood to mean that a specific feature, advantage, or characteristic described in connection with an embodiment is included in at least one embodiment of the present disclosure. Thus, discussion of the features and advantages, and similar language, throughout this specification may, but do not necessarily, refer to the same embodiment.

Furthermore, the described features, advantages, and characteristics of the subject matter of the present disclosure may be combined in any suitable manner in one or more embodiments. One skilled in the relevant art will recognize that the subject matter may be practiced without one or more of the specific features or advantages of a particular embodiment. In other instances, additional features and advantages may be recognized in certain embodiments that may not be present in all embodiments. These features and advantages will become more fully apparent from the following description and appended claims, or may be learned by the practice of the subject matter as set forth hereinafter.

BRIEF DESCRIPTION OF THE DRAWINGS

In order that the advantages of the subject matter may be more readily understood, a more particular description of the subject matter briefly described above will be rendered by reference to specific embodiments that are illustrated in the appended drawings. Understanding that these drawings depict only typical embodiments of the subject matter and are not therefore to be considered to be limiting of its scope, the subject matter will be described and explained with additional specificity and detail through the use of the drawings, in which.

DETAILED DESCRIPTION

Figure 1:
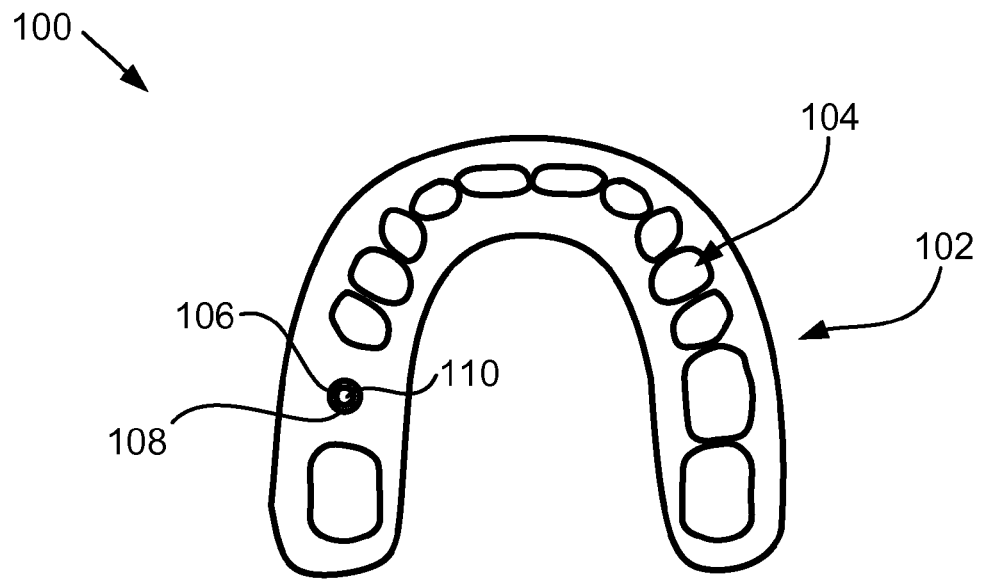
FIG. 1 is a top plan view of a guide splint of a dental implant system according to one embodiment.

Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Additionally, instances in this specification where one element is "coupled" to another element can include direct and indirect coupling. Direct coupling can be defined as one element coupled to and in some contact with another element. Indirect coupling can be defined as coupling between two elements not in direct contact with each other, but having one or more additional elements between the coupled elements. Further, as used herein, securing one element to another element can include direct securing and indirect securing. Additionally, as used herein, "adjacent" does not necessarily denote contact. For example, one element can be adjacent another element without being in contact with that element.

Furthermore, the details, including the features, structures, or characteristics, of the subject matter described herein may be combined in any suitable manner in one or more embodiments. One skilled in the relevant art will recognize, however, that the subject matter may be practiced without one or more of the specific details, or with other methods, components, materials, and so forth. In other instances, well-known structures, materials, or operations are not shown or described in detail to avoid obscuring aspects of the disclosed subject matter.

Generally, described herein are embodiments of a cannulated dental implant system and associated methods. In one embodiment, the dental implant system includes a guide splint, a guide wire, and a series of cannulated drill bits each of a different size. The guide splint is formed using a guide splint formation device and includes a guide sleeve with a guide channel for receiving, positioning, and orienting the guide wire. With the guide splint in place within a patient's mouth, the guide wire is driven into the patient's bone at a desired location using the guide splint. The guide splint is removed leaving the guide wire in place. The cannulated drill bits are then individually and consecutively placed over the guide wire and actuated to incrementally form a hole of a desired size in the bone. In an alternative embodiment, instead of a guide wire and a series of cannulated drill bits, a series of variably sized guide sleeves in conjunction with variably sized drill bits are used to form the hole in the bone.

One representative embodiment of a dental implant system 100 is shown in FIGS. 1-8. The dental implant system 100 includes a guide splint 102 having an impression 104 of a patient's teeth and gums. In this manner, the guide splint 102 is adapted fit over a set of teeth of the patient, e.g., to mate with the teeth and gums of the patient. In other words, the teeth and gums of the patient are received in or mate with the impression 104 formed in the guide splint 102. In one implementation, the guide splint 102 is formed by introducing, such as by pouring, pressing, or otherwise exposing, a malleable material, such as a heated acrylic or plastic, over a cast of the patient's mouth. The malleable material is then allowed to harden over time. The cast of the patient's mouth, e.g., set of teeth, can be made using any of various casting techniques known in the art.

Figure 2:
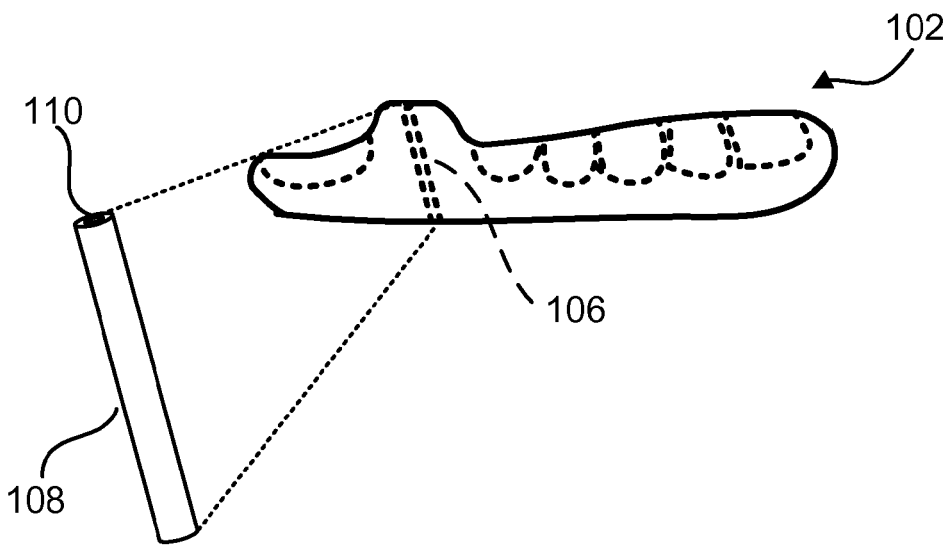
FIG. 2 is a side elevation view of the guide splint of FIG. 1 showing a guide sleeve in more detail.

As shown in FIGS. 1 and 2, the guide splint 102 includes a guide hole 106 formed in the splint at a location or position corresponding with the desired location or position of a dental implant. Further, the orientation, e.g., angle or direction, of the guide hole 106 corresponds with the desired orientation of the dental implant. Generally, the guide hole 106 is formed by drilling a hole into the guide splint 102 using a drilling device, such as drilling assembly 170 described below in association with FIG. 8.

The guide splint 102 also includes at least one embedded guide sleeve 108. In some implementations, the guide sleeve 108 is embedded in the guide splint 102 by inserting the guide sleeve into the guide hole 106. The size of the guide hole 106 corresponds with the size of the guide sleeve 108. In this manner, when retained within the guide hole 106, the position and orientation of the guide sleeve 108 correspond with the desired position and orientation of the dental implant. The guide sleeve 108 is retained within the guide hole 106 via an adhesive, a press-fit connection, a thermal technique, or other technique known in the art. In some implementations, the guide sleeve 108 is permanently retained within the guide hole 106. In other implementations, as will be described in more detail below, the guide sleeve 108 is removably retained within the guide hole 106. Preferably, the guide sleeve 108 has a generally tubular shape. However, the guide sleeve 108 can have any of various shapes as desired. Further, the guide sleeve 108 can be made from any of various materials, such as plastic or metal.

The guide sleeve 108 includes a guide channel 110 extending along a length of the guide sleeve. The guide channel 110 is sized and shaped to matingly receive a guide pin 120 (see FIG. 5). In the illustrated embodiment, the guide pin 120 is generally cylindrically shaped. Accordingly, the guide channel 110 in the illustrated embodiment is a generally cylindrically shaped channel extending coaxially along the length of the guide sleeve 108. However, in other embodiments, the guide pin 120 can have any of various other cross-sectional shapes, such as square, rectangular, triangular, and hexagonal, and the guide channel 110 can be an elongate channel defining a corresponding cross-sectional shape.

Figure 3A:
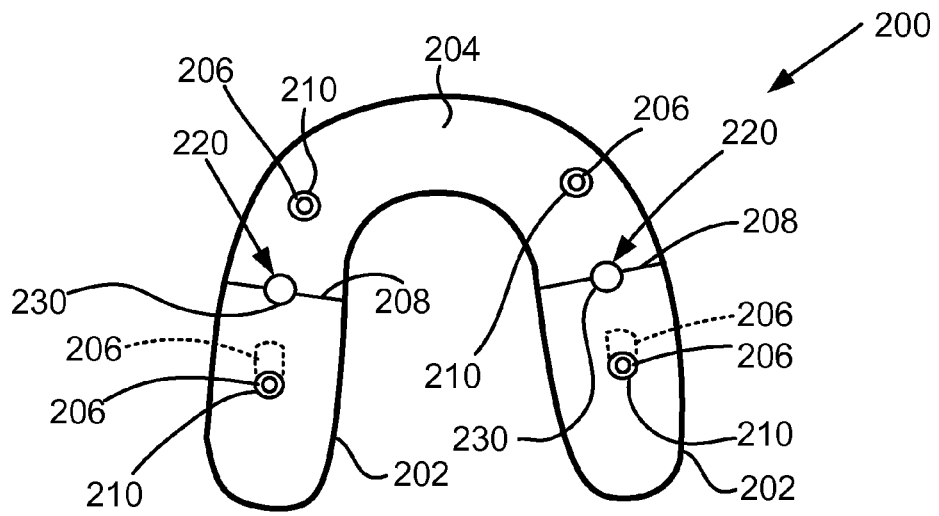
FIG. 3A is a top plan view of a guide splint of a dental implant system according to another embodiment.
Figure 3B:
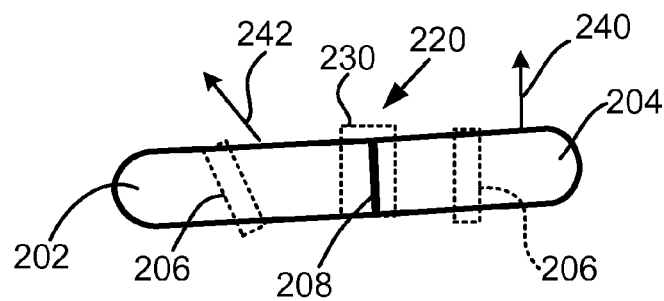
FIG. 3B is a side elevation view of the guide splint of FIG. 3A.

Referring to FIG. 3A, the system 100 can include a guide splint 200 similar to guide splint 102, but having two separable and connectable portions 202, 204, as well as multiple guide sleeves 206. As illustrated, the guide splint 200 is a splint used for installing denture implants. As such, the guide splint 200 includes only an impression of the patient's gums and does not include an impression of the patient's teeth as a patient being fitted for dentures typically does not have teeth. In alternative embodiments for installing non-denture implants, the guide splint 200 includes an impression of the patient's teeth. The portions 202, 204 are connectable along a cut 208 dividing the guide splint 200 into the three portions (i.e., a front portion 202 and two rear portions 204). Generally, the guide splint 200 can be used when multiple implants are being implanted at different angles, i.e., non-parallel orientations. For example, referring to FIG. 3B, the guide sleeves 206 in the front portion 202 are substantially vertically oriented and the guide sleeves 206 in the rear portions 204 are substantially diagonally oriented.

Figure 4:
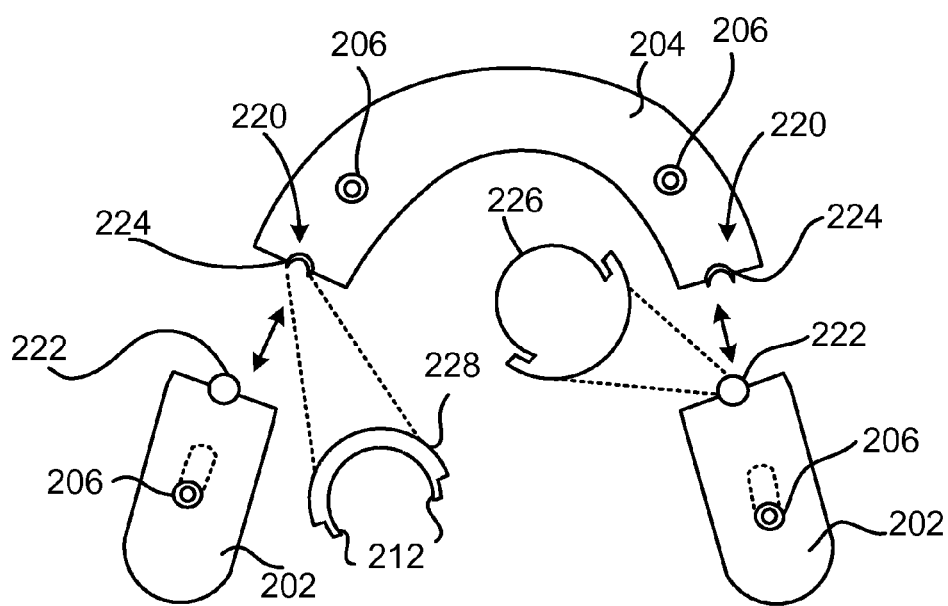
FIG. 4 is an exploded top plan view of the guide splint of FIG. 3A.

The portions 202, 204 are coupled to each other via one or more coupling or engagement mechanisms 220 configured to removably retain the portions 202, 204 against each other. Referring to FIG. 4, each engagement mechanism 220 includes a first portion 222 secured to one of the guide splint portions, e.g., a respective one of the rear portions 202, and a second portion 224 secured to the other of the guide splint portions, e.g., the front portion 204. The first portion 222 of the engagement mechanism 220 is engageable with the second portion 224 of the engagement mechanism to removably retain the two portions 202, 204 of the guide splint 200 together. Similarly, the first and second portions 222, 224 of the engagement mechanism 220 are disengageable with each other to separate the two portions 202, 204 of the guide splint 200.

The first and second portions 222, 224 of the engagement mechanisms 220 can be integrally formed in the splint guide 200 or secured to respective holes 230 formed in the splint guide 200 using an adhesive or bonding technique known in the art. As shown, the cut 208 extends through the holes 230 to split the holes into two portions. The first and second portions 222, 224 of each engagement mechanism 220 can have any of various configurations for facilitating a removable connection, such as a snap-fit connection. As one specific example, the engagement mechanisms 220 illustrated in FIG. 4 utilize a ball-in-socket or snap-fit approach for removably connecting the two portions 202, 204 of the guide splint 200. More specifically, the first portion 222 includes a circular male component 226 and the second portion 224 includes a semi-annular female component 228 configured to matingly receive the male component 226. At least one of the male and female components 226, 228 includes a resiliently flexible portion configured to flex under pressure from the opposing component. For example, the female component 228 includes resiliently flexible end portions 212 that flex outwardly when contacted by the male component 226 with sufficient force. A maximum distance between the flexible end portions 212 is less than the diameter of the male component 226.

As the male component 226 is inserted into the female component 228 with a force greater than a biasing force of the flexible end portions 212, the flexible end portions flex outwardly from an unbiased state into a biased state until half of the male component 226 is beyond the end portions, at which time the end portions are resiliently biased to return to an unflexed state. In this manner, the male component 226 is snap-fit together with the female component 228. In the unflexed state, the female component 228 wraps around a portion of the male component greater than one half of its circumference such that the male component 226 is retained within the female component 228 and the first portion 202 of the guide splint 200 is secured to the second portion 204 to effectively form one piece. When separation of the guide splint 200 is desired, the male component 226 can be pulled against the flexible end portions 212 of the female component 228 with a force greater than the biasing force of the flexible end portions 212 such that the end portions flex to allow the male component 226 to be removed from engagement with the female component 228.

Although the guide splint 200 includes two separable portions 202, 204 with two engagement mechanisms 220, in other embodiments, a guide splint with separable portions can include three or more separable portions with one or more than two engagement mechanisms as desired.

Figure 5:
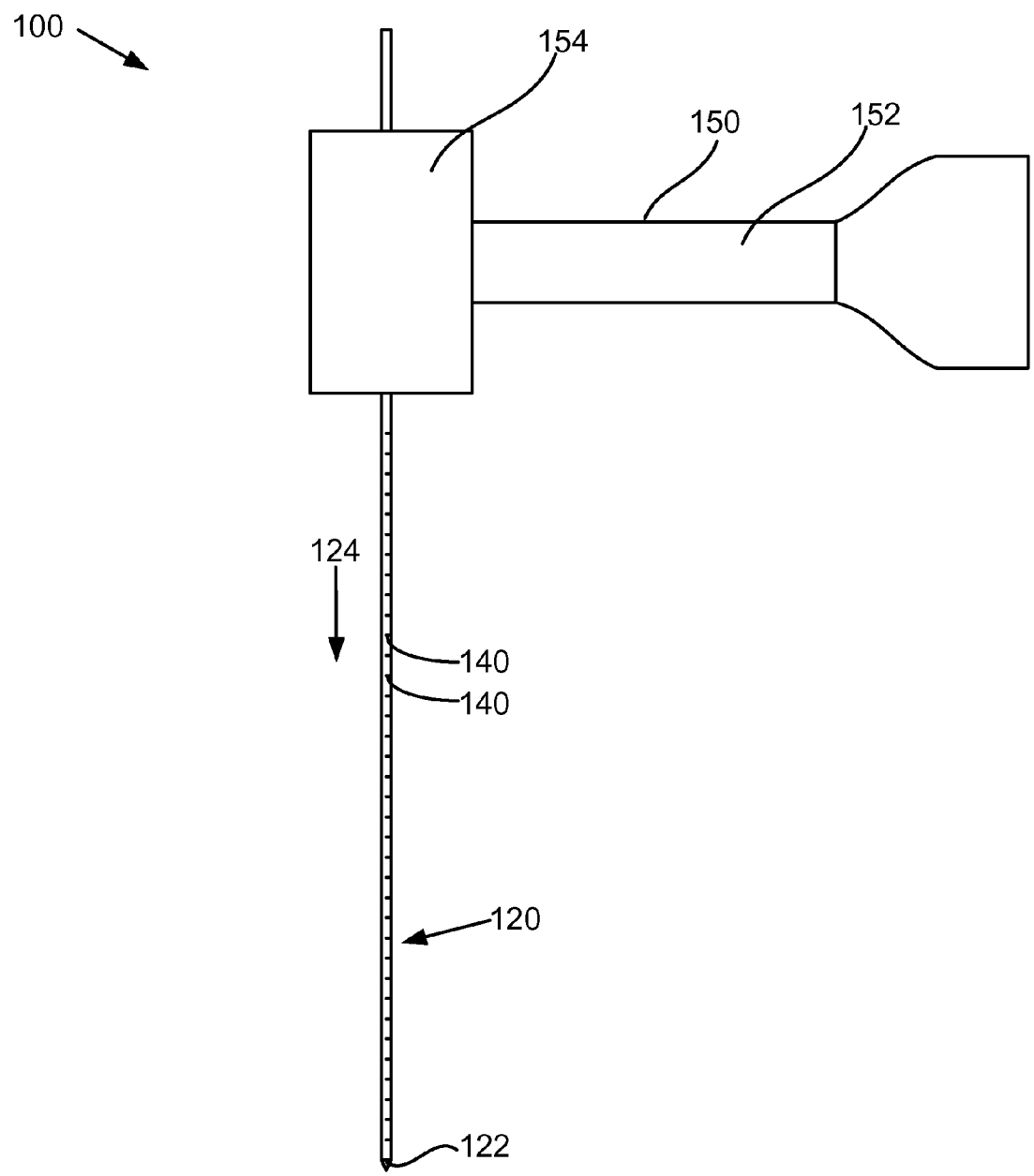
FIG. 5 is a side elevation view of a guide pin and pin driving device of a dental implant system according to one embodiment.
Figure 6A:
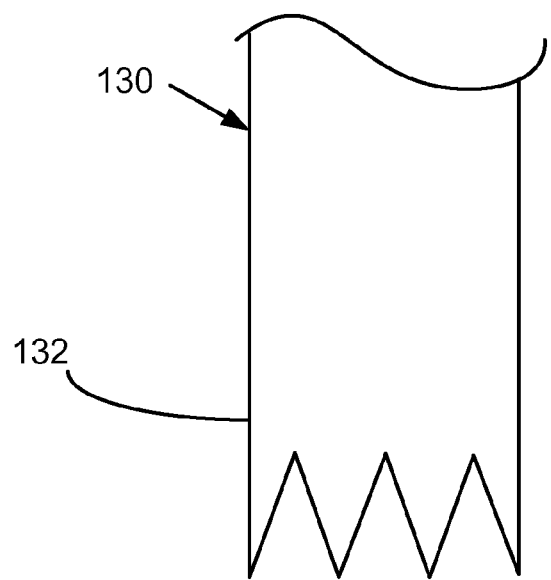
FIG. 6A is side elevation view of a bone penetrating end portion of a guide pin according to one embodiment.

Referring to FIG. 5, the guide pin or wire 120 includes a thin elongate length of an at least partially rigid material, such as metal. The material can be formed in a substantially cylindrical shape as shown, or in any of various other shapes as desired. The guide pin can have any of various width-to-length ratios substantially less than one. In certain implementations, the guide pin 120 has a width of approximately 0.5 mm and a length between approximately 15 mm and approximately 25 mm. In one implementation, the guide pin 120 is sized to fit a 2.0 mm drill. The guide pin 120 includes a bone penetrating end portion 122 configured to penetrate bone tissue and anchor the guide pin to the bone tissue. The bone penetrating end portion 122 can converge into a single sharp point as shown in FIG. 3. In other embodiments, the guide pin includes a jagged edge with several sharp points or teeth for facilitating penetration into and a secure attachment to the bone tissue. For example, as shown in FIG. 6A, a guide pin 130 includes a bone penetrating end portion 132 having a series of sharp teeth each extending from a flat end of the guide pin.

Figure 6B:
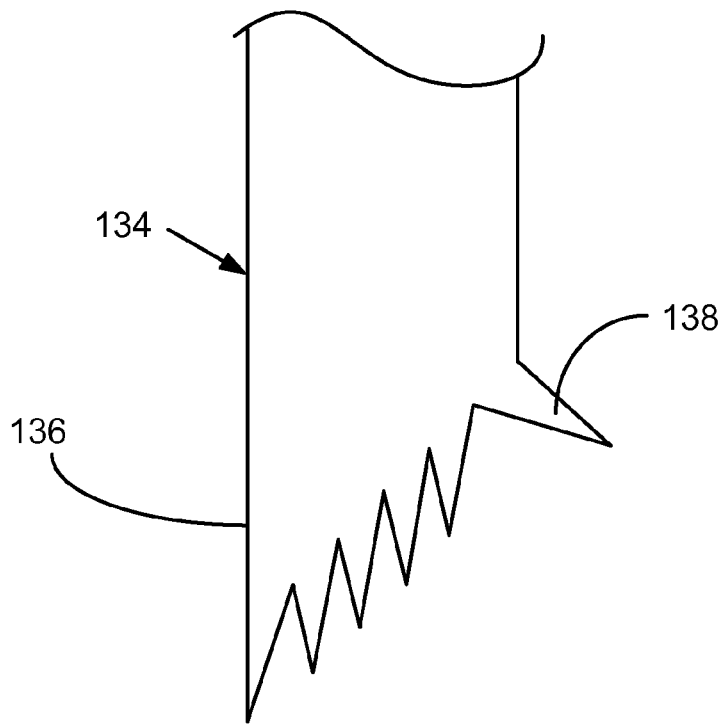
FIG. 6B is a side elevation view of a bone penetrating end portion of a guide pin according to another embodiment.

Alternatively, as shown in FIG. 6B, a guide pin 134 includes a bone penetrating end portion 136 having a series of sharp teeth each extending from an angled end of the guide wire. The angled configuration of the bone penetrating end portion 136 promotes penetration of the guide pin 134 into and secure attachment of the guide pin to relatively steeply angled bone tissue. The sharp teeth can each extend away from the end of the guide pin in a generally lengthwise direction relative to the guide pin as is indicated by direction arrow 124. However, one or more of the sharp teeth can extend away from the end of the guide pin in a direction angled with respect to the lengthwise direction of the guide pin. For example, bone penetrating end portion 136 includes an angled tooth 138 extending away from the end of the guide pin in a direction forming an angle greater than zero and less than ninety with respect to the lengthwise direction. The angled tooth 138 may provide more penetration into steeply angled bone tissue than non-angled teeth to more firmly anchor the guide pin 134 to the bone.

In certain embodiments, the guide pin 120 includes indicia 140 of depth along a length of the guide pin. As will be described in more detail, the indicia 140 are used to determine how far the guide pin has penetrated the bone tissue and how deep a drill bit has penetrated the bone tissue, e.g., the depth of the drilled hole. The indicia 140 can be markings spaced an equal distance, e.g., 1 mm, apart from each other along a length of the guide pin 120 beginning at an end of the bone penetrating portion 122. Each mark can indicate numerically the distance away from the end of the bone penetrating portion 122. The indicia 140 can be formed in or placed on the outer surface of the guide pin 120 using any of various techniques known in the art, such as etching, printing, laminating, and cutting.

The guide pin 120 has relatively smooth sides and is configured to be driven into bone tissue with or without rotation. Accordingly, penetration of the guide pin 120 does not tear or damage surrounding gingival tissue. Referring to FIG. 5, the dental implant system 100 includes a guide pin driver 140 for driving the guide pin into bone tissue. The guide pin driver 150 includes a handle portion 152 coupled to a driving portion 154. The handle portion 152 can be configured to attach to a standard E-type implant motor and the driving portion 154 can include a friction grip, such as contained in K-wire drivers commonly known in the art. The driving portion 154 rotates the guide pin 120 by actuating the friction grip. As the guide pin 120 is rotating, the practitioner drives the guide pin 120 into the bone by grasping and pushing against the handle portion 152. Rotation of the guide pin 120 facilitates insertion of the guide pin into the bone. As the driving portion 154 nears or comes in contact with the bone during the guide pin 120 insertion process, rotation of the guide pin 120 can be halted and the friction grip can be released. This allows the practitioner to slide the driving portion 154 up the guide pin, re-secure the friction grip to the guide pin, and continue with the insertion process without impedance from the driving portion.

Figure 13:
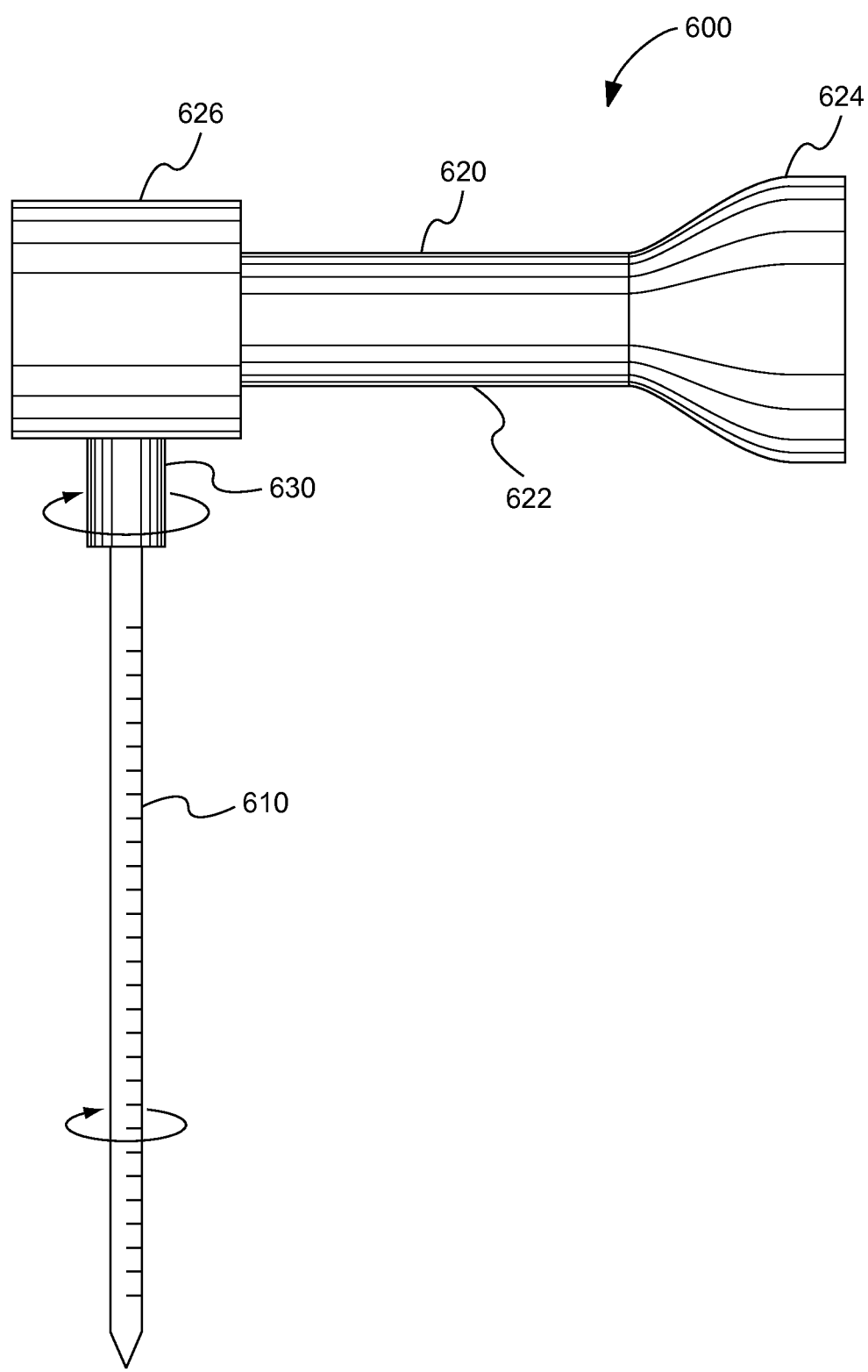
FIG. 13 is a side elevation view of a guide pin and an implant drill driver of a dental implant system according to another embodiment.
Figure 14A:
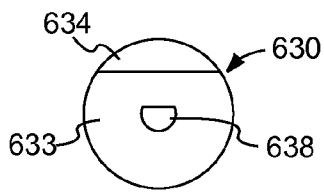
FIG. 14A is a top view of a shank of a dental implant system according to one embodiment.
Figure 15A:
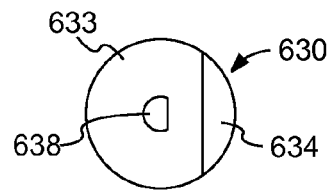
FIG. 15A is a top view of the shank of FIGS. 14A-C.

Referring to FIG. 13, according to an alternative embodiment, a dental implant system 600 includes a conventional implant drill driver 620 for driving both a guide pin 610 and implant drill bits into bone tissue. The guide pin driver 620 includes a handle portion 622 coupled to a motor coupling portion 624 at one end and a driving portion 626 at another end. The motor coupling portion 624 can be configured to attach to a standard E-type implant motor and the driving portion 626 can include a standard latch-type shank connection. In other implementations, the motor coupling portion 624 can be configured to other standard or non-standard implant motors, and the driving portion 626 can include any of various standard or non-standard shank connections.

The dental implant system 600 also includes a shank 630 configured to co-rotatably couple the guide pin 610 to the implant drill driver 620 (e.g, the driving portion 626 of the implant drill driver). Referring to FIGS. 14A-C and 15A-C, the shank 630 has an elongate body 631 extending from a proximal end 633 to a distal end 635. As shown, the elongate body 631 is substantially cylindrical with a circular cross-sectional shape. However, in other embodiments, the elongate body can have any of various cross-sectional shapes.

The shank 630 includes a latch engagement portion 632 near the proximal end 633 that includes features configured to facilitate a secure connection to the latch-type shank connection of the driving portion 626 of the implant drill driver 620. For example, the latch engagement portion 632 includes a circumferential channel 635 and a notch or keyed-in section 634. The notch 634 extends axially from the proximal end 633, through the latch engagement portion 632, and to an intermediate location between the proximal and distal ends 633, 635. The latch-type shank connection of the driving portion 626 of the implant drill driver includes a channel engaging feature (not shown) that engages the channel 635 to prevent axial movement of the shank 630 relative to the driver 620. In other words, engagement between the channel engaging feature of the driving portion 626 and the channel 635 prevents separation of the shank 630 from the driver 620. The latch-type shank connection of the driving portion 626 also includes a notch engaging feature (not shown) that mates with the notch 634 to facilitate co-rotation of the shank 630 and a driving member (e.g., rotating member) of the driving portion 626.

In alternative embodiments, the shank 630 can have different driver engaging features than those illustrated to accommodate a driver that uses a different type of connection. Generally, the driver engaging features can be any of various types of features depending on the configuration of the driver.

In certain implementations, the driver engaging features of the shank 630 are the same as the driver engaging features of the implant drill bits and other implant tools usable by the implant drill driver 620. In this manner, the shank 630 is interchangeable with the implant drill bits and other implant tools used by an implant drill driver during a dental implant installation procedure.

The shank 630 also includes an internal passage 638 extending lengthwise through the elongate body 631 from the proximal end 633 to the distal end 635. Preferably, the internal passage 638 extends co-axially relative to a central axis of the shank 630. The internal passage 638 has a non-round cross-sectional shape. In the illustrated embodiment, the internal passage 638 has a substantially D-shaped cross-sectional shape. However, in other embodiments, the internal passage 638 can have any of various other non-round cross-sectional shapes, such as, for example, triangular, rectangular, polygonal, elliptical, and the like. Although the internal passage 638 extends completely through the elongate body 631 in the illustrated embodiment, in other embodiments, the internal passage 638 may extend from the distal end 635 to an intermediate location along the length of the body between the distal end and the proximal end 633.

Figure 16A:
FIG. 16A is a top view of a guide pin having a notched section according to one embodiment.
Figure 14B:
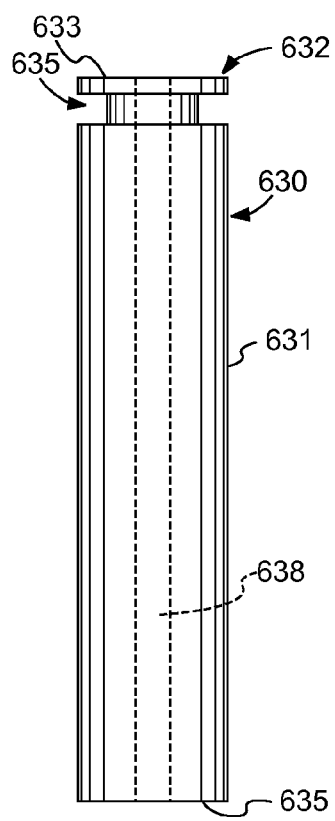
FIG. 14B is a front view of a shank of a dental implant system according to one embodiment.
Figure 15B:
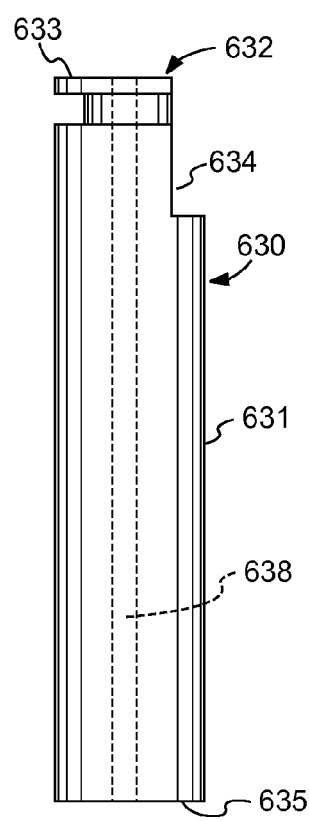
FIG. 15B is a side view of the shank of FIGS. 14A-C.
Figure 16B:
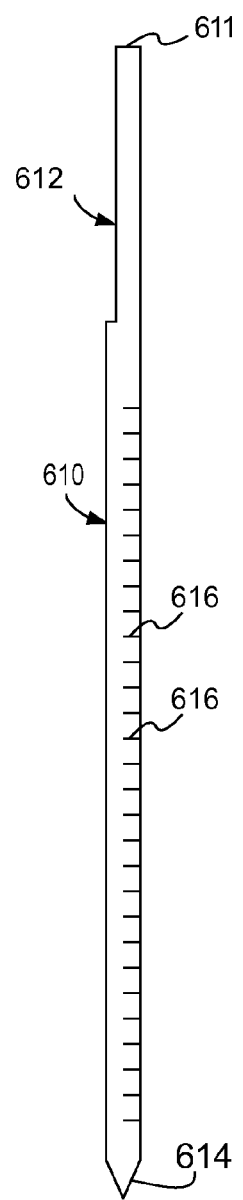
FIG. 16B is a side view of a guide pin having a notched section according to one embodiment.
Figure 14C:
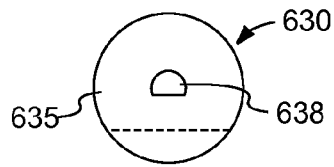
FIG. 14C is a bottom view of a shank of a dental implant system according to one embodiment.
Figure 15C:
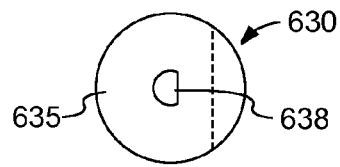
FIG. 15C is a bottom view of the shank of FIGS. 14A-C.

Referring now to FIGS. 16A-B, the guide pin 610 includes features similar to the features of guide pin 120. For example, the guide pin 610 is formed of a thin elongate length of an at least partially rigid material, such as metal, and has a bone penetrating end portion 614 configured to penetrate bone tissue and anchor the guide pin to the bone tissue. Like the guide pin 120, in certain implementations, the guide pin 610 can include indicia 616 of depth along a length of the guide pin and preferably is fluteless along its length. However, unlike the guide pin 120, the guide pin 610 includes a shank engagement portion 612 opposite the bone penetrating end portion 614. The shank engagement portion 612 extends lengthwise from a proximal end 611 of the guide pin 610. Further, the shank engagement portion 612 includes a notched or keyed-in section that has a cross-sectional shape corresponding with the cross-sectional shape of the internal passage 638 of the shank 630. More specifically, the cross-sectional shape of the shank engagement portion 612 is non-round and matches the non-round cross-sectional shape of the internal passage 638. The corresponding non-round shapes of the shank engagement portion 612 and the internal passage 638 facilitates co-rotation between the engagement portion (i.e., the guide pin 610) and the internal passage 638 (i.e., the shank 630) as shown in FIG. 13. The shank engagement portion 612 is sized slightly smaller than the internal passage 638 to facilitate insertion of the shank engagement portion into the internal passage, as well as mateable engagement between the shank engagement portion and the internal passage. The cross-sectional size of the guide pin 610 between the shank engagement portion 612 and the bone penetrating end portion 614 is larger than the internal passage 638 thereby providing a stop at the base of the shank engagement portion.

In certain implementations, the relative sizes of the shank engagement portion 612 and the internal passage 638 allow for relatively minimal interference between the engagement portion and internal passage such that the shank engagement portion is freely slidable into and out of the internal passage 638. In these implementations, the engagement portion 612 is retained within the internal passage 638 during use by the opposing forces applied the guide pin 610 from the bone material or other tissue and the driver 620.

In certain other implementations, the internal passage 638 and shank engagement portion 612 are sized to allow for slight frictional interference between the passage and the shank engagement portion. By introducing a slight frictional interference, the shank engagement portion 612 can be at least partially frictionally retained within the internal passage 638 to reduce inadvertent separation of the guide pin 610 from the shank 630. In one implementation, to facilitate frictional engagement between the internal passage 638 and the guide pin 610, the shank engagement portion 612 tapers (e.g., diverges in a direction away from the proximal end 611) from a cross-sectional area smaller than the internal passage to a cross-sectional area larger than the internal passage. In this latter implementation, as the shank engagement portion 612 is inserted into the internal passage 638, the tapered engagement portion eventually frictionally interferes with the wall of the internal passage to frictionally retain the engagement portion within the internal passage. Alternatively, the internal passage 638 can be tapered and the shank engagement portion can be non-tapered to facilitate frictional engagement. In yet other embodiments, the shank 630 can be equipped with set screws or other similar retention devices to removably retain the shank engagement portion 612 within the internal passage.

For use, the shank engagement portion 612 is inserted (e.g., slidably inserted) into the internal passage 638 and the bone penetrating end portion 614 of the guide pin 612 is positioned on tissue at an implant installation site. The implant drill driver 620 is then actuated to rotate the shank 630. As the shank 630 rotates, the engagement between the non-round shank engagement portion 612 and the internal passage 638 causes the guide pin 610 to co-rotate with (e.g., rotate at the same rate as) the rotating shank. With the guide pin 610 rotating, a practitioner drives the guide pin into the bone by grasping and pushing against the handle portion 622. Once the guide pin 610 is satisfactorily driven into the bone tissue of a patient, the implant drill driver 620 can be moved away from the guide pin 610 to slide the shank engagement portion out from within the internal passage 638 and disengage the driver from the guide pin. In certain alternative embodiments, disengagement between the driver 620 and the guide pin 612 may require loosening set screws or other fastening devices. The shank 630 can then be removed from the connection of the implant drill driver 620 and a cannulated drill bit can be removably coupled to the same connection of the implant drill driver. Then, the cannulated drill bit is positioned such that the driven guide pin extends up through the drill bit and the implant drill driver is actuated to rotate the drill bit and drill the bone tissue.

The dental implant system 600 provides certain advantages over the dental implant system 100 because the same driver 600 can be used to drive both a guide pin and the associated drill bits, whereas the dental implant system 100 may require two separate drivers (e.g., a guide pin driver and an implant drill driver) to drive the guide pin and drill bits during a dental implant installation procedure. For example, once used to drive a guide pin into bone tissue, the shank 630 can be removed and interchanged with a cannulated drill bit to begin the drilling stage of the dental implant installation without the need to switch to a separate driver. Additionally, the dental implant system 600 improves the drivability (e.g., rotational efficiency) of a guide pin because the non-round coupling between the internal passage of the shank and the shank engagement portion of the guide pin avoids the need for a friction-grip-type coupling (which can be inefficient due to slipping between round components).

Although the dental implant system 600 has been described as being associated with dental applications, and more particularly to dental implant installation procedures, the features and advantages associated with the dental implant system 600 are equally applicable to non-dental applications, as well as dental applications not involving the installation of dental implants. For example, the dental implant system 600 can be used to drill holes in bone tissue at any of various locations within the body (e.g., arms, legs, feet, joints, etc.) and not just bone tissue associated with the mouth.

Figure 7C:
FIG. 7C is a side elevation view of a cannulated drill bit of a large size engaged with the guide pin according to one embodiment.
Figure 7B:
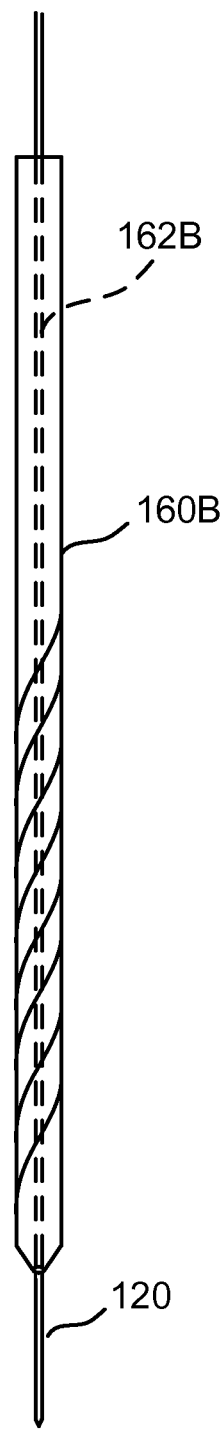
FIG. 7B is a side elevation view of a cannulated drill bit of a medium size engaged with the guide pin according to one embodiment.
Figure 7A:
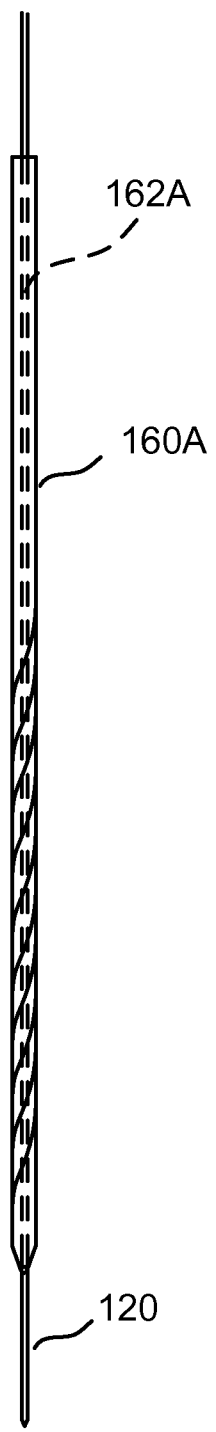
FIG. 7A is a side elevation view of a cannulated drill bit of a small size engaged with a guide pin according to one embodiment.

Referring to FIGS. 7A-7C, the dental implant system 100 includes two or more cannulated drill bits, such as drill bits 160A-160C, each sized to drill a differently sized cylindrical hole in bone tissue. As illustrated, drill bit 160A of FIG. 7A is smaller, i.e., has a smaller outer diameter, than drill bit 160B of FIG. 7B and drill bit 160B is smaller than drill bit 160C of FIG. 7C. Accordingly, drill bit 160A is configured to form a cylindrical hole smaller than a hole formed by drill bit 160C, and drill bit 160B is configured to form a cylindrical hole smaller than a hole formed by drill bit 160C. Generally, the diameter of the holes formed by the drill bits corresponds with the outer diameter of the respective drill bits. The drill bits can have straight or tapered shanks, and have any of various spirals, point angles, and lip angles appropriate for drilling bone tissue.

Each drill bit 160A-160C includes a respective channel 162A-162C through which the guide pin 120 is extendable. The channels 162A-162C extend coaxially along the entire length of the respective drill bits 160A-160C. When extended through the channels 162A-162C, the guide pin 120 is configured to guide the drill bits 160A-160C in a direction parallel to the lengthwise direction 124 of the guide pin. Accordingly, the cross-sectional areas of the channels 162A-162C closely match the cross-sectional area of the guide pin 120. For example, the diameters of the channels 162A-162C are just larger than the diameter of the guide pin 120. In this manner, when the guide pin 120 is extended through the channels 162A-162C, the axes of the drill bits 160A-160C are substantially coaxial with the axis of the guide pin 120. Maintaining coaxial alignment of the drill bits 160A-160C with a guide pin 120 anchored to bone tissue ensures the drill bits enter the bone tissue at the same orientation as the guide pin and at a desired location.

Figure 8:
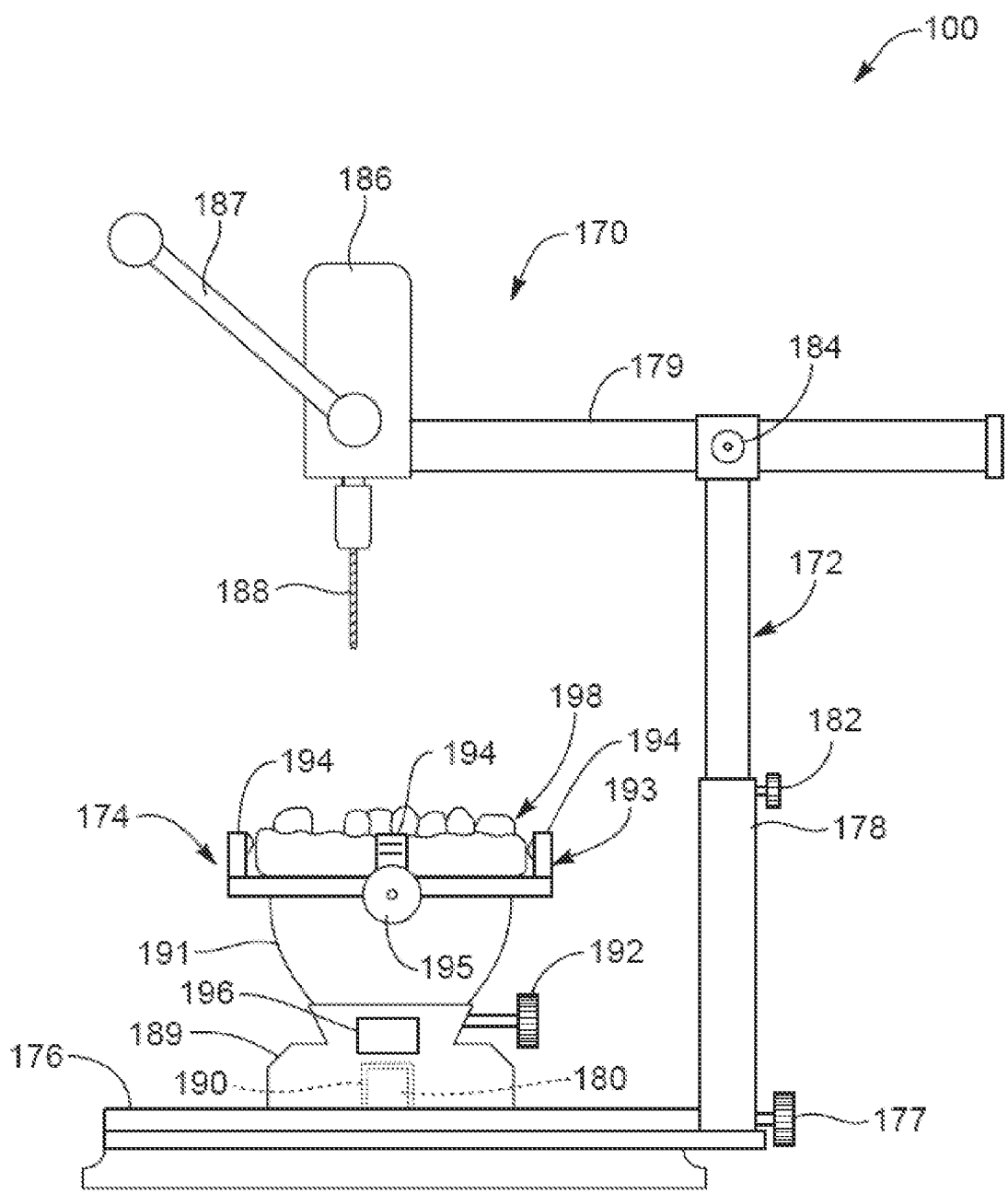
FIG. 8 is a side elevation view of a drilling assembly according to one embodiment.

As shown in FIG. 8, the dental implant system 100 includes a drilling apparatus 170 or splint formation device configured to facilitate precise positioning and orientation of the guide sleeve 108 in the splint 102. The drilling apparatus 170 includes a drill press 172 removably coupled to an alignment stand 174.

The drill press 172 includes a base 176 and a vertical arm 178 pivotable about the base 176. The vertical arm 178 includes a telescoping member adjustable to change the height of the vertical arm. When the vertical arm 178 is adjusted to a desired angle with respect to the base 176 and the height of the vertical arm 178 is adjusted to a desired height, the locks 177, 182 can be tightened to secure the vertical arm at the desired angle and height, respectively. The drill press 172 also includes a horizontal arm 179 coupled to a drill bit driving assembly 186. The horizontal arm 179 is adjustable horizontally to move the driving assembly 186 toward and away from the vertical arm 178. When the drill bit driving assembly 186 is in a desired location with respect to the base 176, the horizontal arm 179 can be locked into place via a lock 184. The drill bit driving assembly 186 includes a drill bit chuck for securing a drill bit, such as drill bit 188. The drill bit 188 can be raised and lowered relative to the drill bit driving assembly 186 via actuation of a handle 187. In some implementations, the horizontal arm 179 includes markings indicating a distance between the axis of the drill bit 188 and an origin, e.g., geometric center, of the base 176. The drill press 172 includes a locking key 180 protruding from and fixed relative to the base 176. In certain implementations, the locking key 180 is positioned at the origin of the base 176.

The alignment stand 174 includes a base 189 having a notch 190 formed therein. The notch 190 is configured to matingly engage the key 180 of the drill press 172 to removably secure the alignment stand 174 in a predetermined position and orientation relative to the base 176. In certain implementations, the notch 190 is matingly engaged with the key 180 by sliding the notch over the key. In this manner, the position and orientation of the alignment stand 174 relative to the base 176 can be reliably reproduced during the guide sleeve forming process. The base 189 pivotally receives a ball-shaped, e.g., semi-spherically-shaped, component 191. The alignment stand 174 includes a clamp 193 secured to the ball-shaped component 191 that is movable, e.g., pivotably relative to the base 189. The clamp 193 includes at least three adjustable arms 194 for securing a cast, such as cast 198. The arms 194 can be tightened against and loosened from the cast by rotating the adjustment knob 195. The orientation of the ball-shaped component 191, and thus the orientation of the clamp 193 and a cast secured to the clamp, is adjustable into any of an infinite number of orientations by rotating or pivoting the component 191 relative to the base 189. When the orientation of the cast or splint is in a desired orientation, a lock 192 can be tightened to fix the ball-shaped component 191 relative to the base 189. To facilitate a precise and proper orientation of the cast or splint, the alignment stand 174 can include orientation indicia 196, such as a digital readout, indicating of the orientation of the cast or splint.

Figure 9:
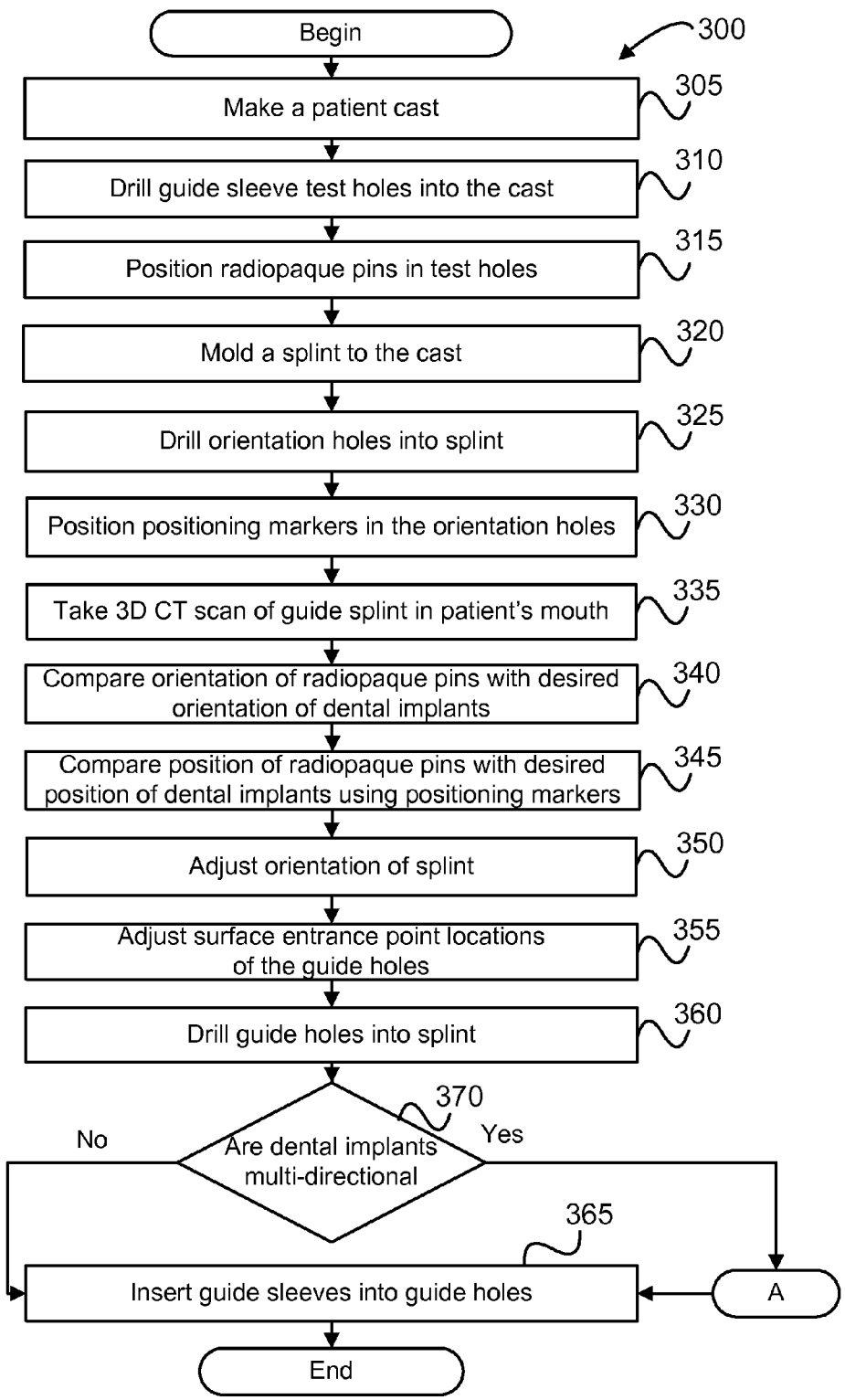
FIG. 9 is a flow chart diagram illustrating a method for forming a guide splint according to one embodiment.

Referring to FIG. 9, a method 300 is shown for forming a guide splint, such as guide splints 102, 200. The method 300 begins by making 305 a cast, e.g., cast 198 of FIG. 8, of the patient's mouth and drilling 310 guide sleeve test holes into the cast at the same location and orientation as the desired location and orientation of the implants using the drilling assembly 100. More specifically, in one example, the cast is secured in the clamp 193 of the alignment stand 174 and the position of the clamp is adjusted into the desired orientation of the dental implant using the ball-shaped component 191. The orientation of the clamp 193 is secured in place by tightening the lock 192. The position of the drill bit driving assembly 186 is then adjusted to place the drill bit 188 in the desired position of the dental implant. Adjustment of the drill bit driving assembly 186 position can be effectuated by rotation of the vertical arm 178 and movement of the horizontal arm 179. With the desired position and orientation of the cast locked into place, the test hole can be drilled into the cast using the handle 187 to lower the drill bit 188 into the cast.

After a desired number of guide sleeve test holes are drilled into the cast, pins made from a radiopaque material, such as metal or plastic, are positioned 315 in the test holes such that a portion of the pins extend above the surface of the cast. The alignment stand 174 is then removed from the drill press 172 with the cast still secured to the stand or the alignment stand can remain coupled to the drill press. The method 300 then includes molding 320 a splint over the cast and pins by pouring or pressing a malleable and hardenable material, such as heated acrylic, onto the cast. The pins are molded into or integrated with the molded splint. After the malleable material hardens, if the alignment stand 174 has been removed for the guide splint molding process, the stand is again secured to the drill press 172 by engaging the notch 190 with the key 180. Orientation holes are then drilled 325 into the splint 102 and radiopaque positioning markers or pins are positioned 330 in the orientation holes. In certain implementations, three orientation holes are drilled 325 into the splint. The three orientation holes include two x-axis holes positioned on approximately opposite sides of the origin of the drill press 172 on an x-axis associated with the origin. The third of the three orientation holes is a y-axis hole positioned on a y-axis associated with the origin. Each of the orientation holes is parallel to each other.

The method 300 includes removing the splint from the cast with the radiopaque markers molded to the splint 102, trimming the radiopaque pins if necessary, placing the splint in the patient's mouth, and taking 335 a medical imaging scan, e.g., a 3D CT scan, of the guide splint in the patient's mouth. In certain implementations, the desired orientation, position, and depth of each dental implant is determined using implant placement software commonly known in the art. Using the 3D CT scan and imaging software, the angulation or orientation of the radiopaque markers are compared 340 with the desired orientation of the implants determined using the implant placement software. Similarly, using the position of the positioning markers shown in the 3D CT scan, the desired position or surface entrance point location of the dental implants are compared 345 with the actual position of the markers. Any discrepancies between the desired orientation of the dental implants and the actual orientation and position of the radiopaque markers are accounted for by adjusting 350 the orientation of the clamp 193. The actual surface entrance point location of the guide hole 106 may also be adjusted 355 based on the comparison 345 between the actual marker position as recorded on a grid of the 3D CT scan and the desired dental implant positions selected using the positioning software by marking the cast 198 using a coordinate system grid sheet. The grid sheet is a clear plastic template with an x-axis and y-axis coordinate grid printed or formed thereon and small holes at each corner of the squares forming the grid. The grid sheet is positioned on the cast 198 (which is secured in the clamp 193 at the desired orientation) such that the x-axis and y-axis of the template is aligned with the orientation holes such that the template effectively mimics the grid of the CT scan. A marking tool can then be inserted into the hole in the grid sheet corresponding to the corrected implant position or entrance site. After the drill bit driving assembly 186 is securely positioned over the corrected entrance site, the guide splint 102 is placed on the cast 198 and the drill bit driving assembly 186 is actuated to drill a hole into the splint at the corrected entrance site.

After the orientation of the clamp 193 is properly adjusted and the surface entrance point location is properly marked for a respective guide hole 106, the method 300 includes drilling 360 guide hole 106 at the adjusted orientation and marked location to a desired depth. In this same manner, a guide hole 106 corresponding to each dental implant is drilled 360. A guide sleeve 108 is then inserted 365 into each guide hole 106.

In an alternative method for forming a guide splint, the method includes only actions 305, 320, 360 and 365 of method 300. In other words, in certain methods, the splint 102 can be formed without using 3D imaging techniques.

Figure 10:
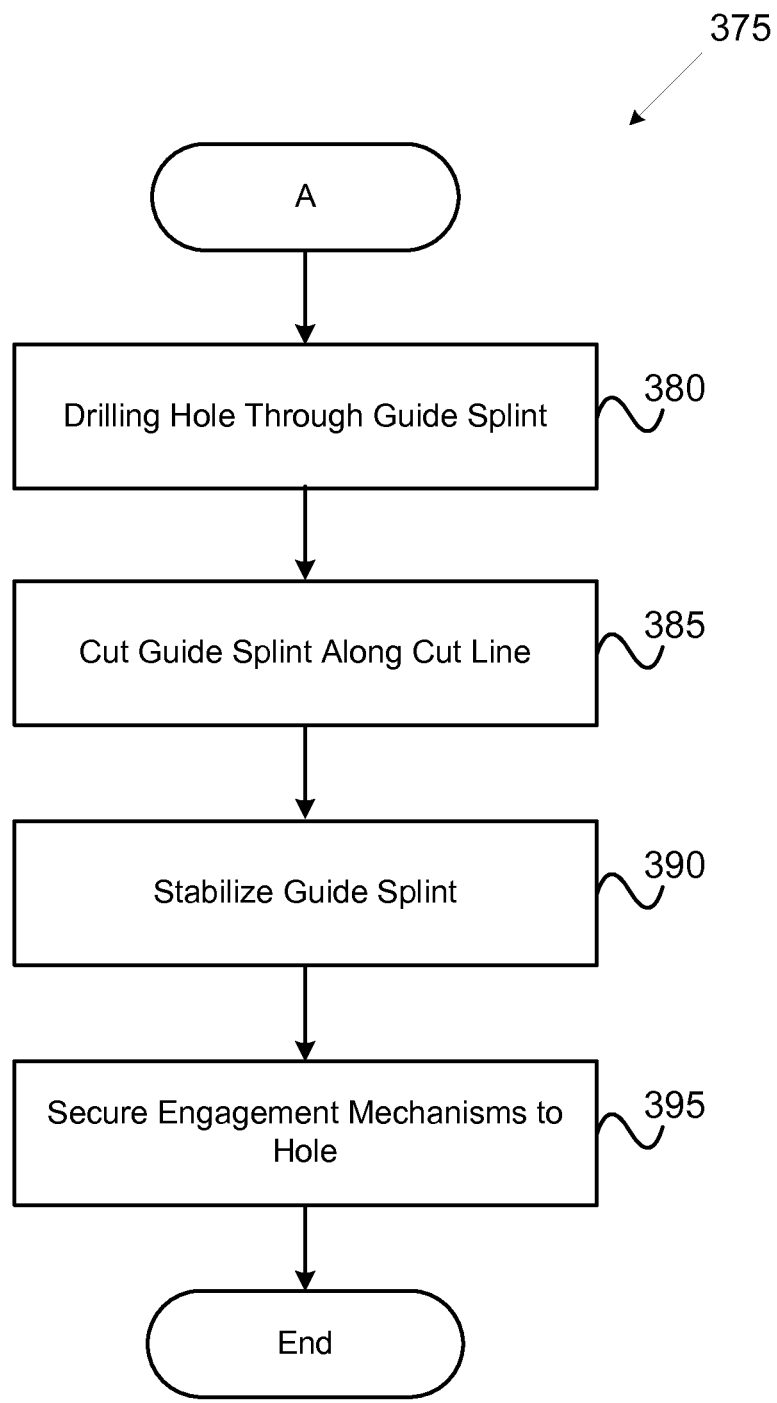
FIG. 10 is a subroutine of the method of FIG. 9 depicting actions associated with forming a separable guide splint.

For situations involving multiple dental implants at multiple orientations, the method 300 can include actions for forming a multidirectional guide splint, such as guide splint 200. If there are no multidirectional dental implants as determined in action 370, then the method 300 proceeds from action 360 to action 365. However, if there are multidirectional dental implants as determined in action 370, the method 300 proceeds to actions associated with method actions 375 (see FIG. 10). With reference to guide splint 200, the subroutine A includes drilling 380 at least one hole 230 through the guide splint. The subroutine A then includes cutting 385 the splint 200 into the at least two portions 202, 204 along the cut line extending through the holes 230. In some embodiments, the cut is configured to extend through the guide holes 210 drilled in the splint. The cut line can be straight as illustrated or curved as desired. After being cut, the splint 200 can be stabilized 390 or temporarily kept together using any of various stabilizing means, such as wax or through use of a clamp. An engagement mechanism, such as mechanisms 220, is then positioned and secured 395 within the holes 230 using any of various techniques, such as placing an adhesive between the mechanisms and the surfaces of the holes 230.

After the guide splint 102, 200 is formed, it can be used to accurately and precisely implant dental implants in a patient's mouth. According to one embodiment, a method 400 for implanting one or more dental implants includes properly placing 405 the guide splint 102, 200 in the patient's mouth over the patient's teeth and gums. The method 400 proceeds by determining 410 whether a cannulated technique or non-cannulated technique is desirable. If a cannulated technique is desired, the method 400 includes driving 415 a guide pin 120 through the channels of each of the guide sleeves 108 and into the bone tissue using the guide pin driver 150. The method 400 then determines whether there are multiple multidirectional dental implants at 420. If there is only a single dental implant or multiple generally parallel dental implants, then the method 400 proceeds to remove 425 the guide splint 102 from the patient's mouth by simultaneously sliding the entire guide splint and guide sleeve(s) along the guide pin(s) away from the implant location(s).

If, however, there are multiple multidirectional dental implants as determined at 420, then the method determines 430 whether the multidirectionality of the dental implants is excessive, e.g., forming at angle of greater than 10 degrees. If the multidirectionality of the dental implants is not excessive, then the guide splint is removed by first removing 435 one or more of the guide sleeves from the guide splint and sliding the guide sleeves along the guide pins away from the guide splint. In this manner, space is created between the guide pins and the respective guide holes, which provides additional maneuverability and lateral freedom for then removing 440 the guide splint from engagement with the guide pins and the patient's mouth. If, however, the multidirectionality of the dental implants is excessive, then the guide splint, e.g., guide splint 200, is removed by separating 445 the guide splint into two or more pieces or portions (e.g., portions 202, 204 of guide splint 200). The portions are then separately removed 450 from the patient's mouth by individually sliding each portion and associated guide sleeve(s) along the associated guide pin(s) away from the implant location(s). In one embodiment, the portion of the guide splint housing the least angled sleeve(s) (e.g., front portion 204 housing vertical sleeves 206) is first removed in a direction away from the patient's gums and parallel to the orientation of the least angled sleeve(s), such as shown by directional arrow 240 in FIG. 3B. Then, the portion or portions housing the more severely angled sleeves (e.g., rear portions 202 housing respective sleeve 206) are subsequently removed in a direction away from the patient's gums and parallel to the orientation of the angled sleeve(s), such as shown by directional arrow 242 in FIG. 3B. Separating the guide splint into one or more portions can provide greater maneuverability and lateral freedom for removing the guide splint from engagement with the guide pins compared with removing just the guide sleeves. In one embodiment, the portions of the guide splint are separated by disengaging engagement elements, e.g., engagement mechanisms 220, that retain the portions together.

After the splint guide has been removed from the patient's mouth following one of the actions 425, 440, 450, the method 400 proceeds to subroutine B. In subroutine B, a first cannulated drill bit, e.g., drill bit 160A, is slid onto the guide pin anchored to the bone tissue and actuated to drill 500 a first hole in the bone tissue. The first hole has a first diameter corresponding to the size of the first cannulated drill bit. The drill bit 160A penetrates the bone tissue to a depth equal to the desired depth of the dental implant. Further, the guide pin guides and stabilizes the drill bit as it drills the first hole. In this manner, the guide pin facilitates the drilling of a hole substantially at a desired position and orientation of the dental implant. After the first hole is drilled 500, the first cannulated drill bit is removed, e.g., slid off of the guide pin, and a second cannulated drill bit, e.g., drill bit 160B, is slid onto the guide pin to drill 510 a second hole in the bone tissue over the first hole. The second cannulated drill bit is larger than the first cannulated drill bit such that the second hole has a larger diameter than the first hole, thus effectively enlarging the resultant hole in the bone tissue. The guide pin guides and stabilizes the second cannulated drill bit such that the second hole is also substantially in the desired position and orientation of the implant. After the second hole is drilled 510, the second cannulated drill bit is removed and a third cannulated drill bit, e.g., drill bit 160C, is slid onto the guide pin to drill 520 a third hole in the bone tissue over the second hole. The third cannulated drill bit is larger than the second cannulated drill bit such that the third hole has a larger diameter than the second hole, thus effectively enlarging the resultant hole in the bone tissue. The guide pin guides and stabilizes the third cannulated drill bit such that the third hole is also substantially in the desired position and orientation of the implant. The third cannulated drill bit is then removed.

The general actions associated with events 510-520 can be repeated, but with incrementally larger cannulated drill bits, until the hole in the bone tissue reaches a desired diameter for implanting the dental implant. Incrementally or gradually increasing the size of the drill bits promotes cleaner and more precise holes, as well as reduces inadvertent chipping of the bone tissue and removal of other tissue adjacent the implant site. After the implant hole reaches the desired diameter, the guide pin anchored in the bone tissue is removed 530. In certain implementations, the guide pin is removed 530 using removal tool, such as a reverse friction grip removal tool. If necessary, the removal tool can be coupled to a ratcheting mechanism for facilitating removal of the guide pin. It is noted that although a method using several incrementally larger cannulated drill bits is shown and provides certain advantages, in other embodiments, a single cannulated drill bit corresponding to the desired diameter for implanting the dental implant can be used.

Figure 11:
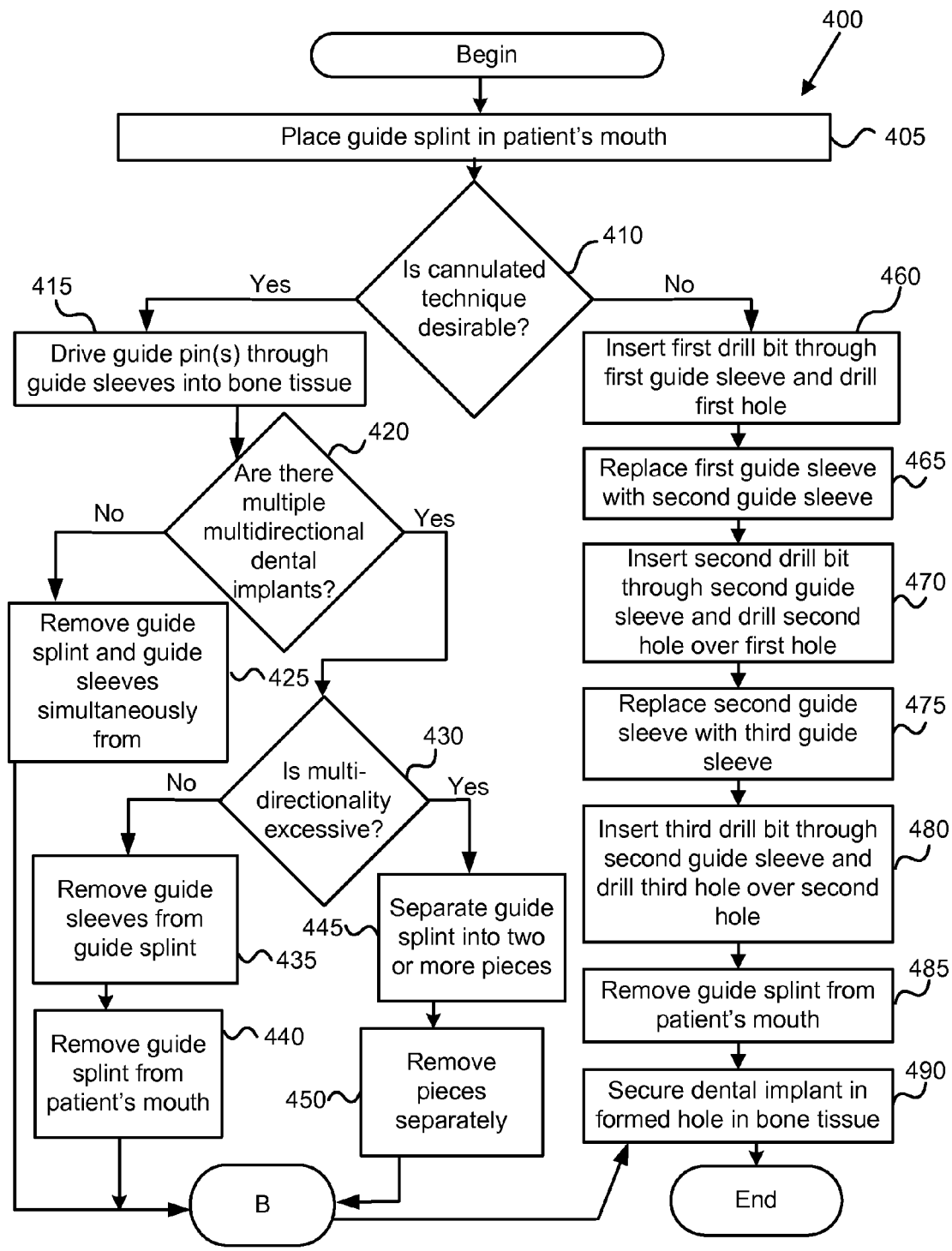
FIG. 11 is a flow chart diagram illustrating a method for implanting one or more dental implants according to one embodiment.
Figure 12:
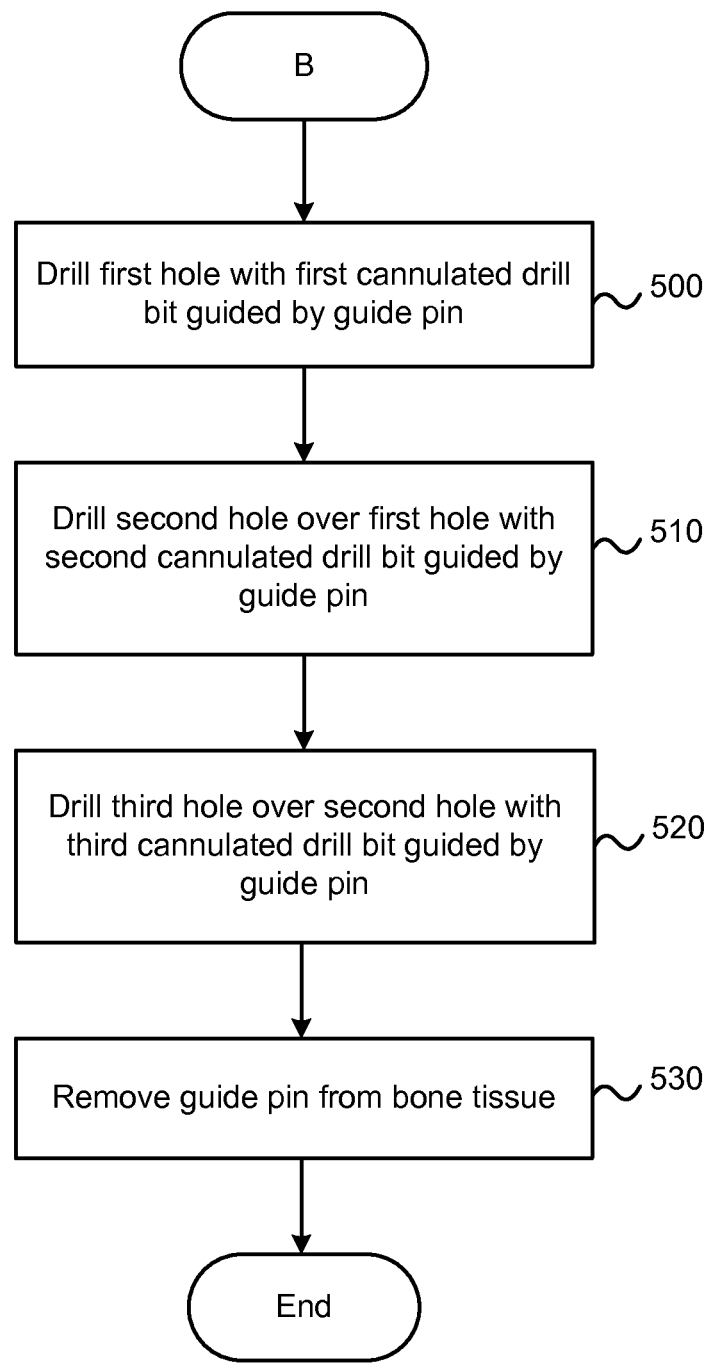
FIG. 12 is a subroutine of the method of FIG. 11 depicting actions associated with a cannulated technique according to one embodiment.

Referring back to FIG. 11, if a cannulated technique is not desirable as determined at action 410, the method 400 proceeds to insert 460 a first drill bit through the first guide sleeve in the guide splint and drill a first hole in the bone tissue. The first drill bit has an outer diameter that closely fits the inside diameter of the guide channel defined by the first guide sleeve. In this manner, the guide sleeve acts to guide and stabilize the first drill bit such that the first hole is substantially in the desired position and orientation of the implant.

After the first hole is drilled, the first drill bit is pulled out of the first guide sleeve. The first guide sleeve is then removed and replaced 465 by a second guide sleeve having a guide channel larger than the guide channel of the first guide sleeve, but an outer diameter the same as the outer diameter of the first guide sleeve. A second drill bit larger than the first drill bit is inserted 470 through the guide channel of the second guide sleeve to drill a second hole over the first hole. The second hole is larger than the first hole such that the first hole is effectively enlarged by the drilling of the second hold. The second drill bit has an outer diameter that closely fits the inside diameter of the guide channel defined by the second guide sleeve. In this manner, the guide sleeve acts to guide and stabilize the second drill bit such that the second hole is substantially in the desired position and orientation of the implant.

After the second hole is drilled, the second drill bit is pulled out of the second guide sleeve. The second guide sleeve is then removed and replaced 475 by a third guide sleeve having a guide channel larger than the guide channel of the second guide sleeve, but an outer diameter the same as the outer diameter of the first and second guide sleeves. A third drill bit larger than the second drill bit is inserted 480 through the guide channel of the third guide sleeve to drill a third hole over the second hole. The third hole is larger than the second hole such that the second hole is effectively enlarged by the drilling of the third hold. The third drill bit has an outer diameter that closely fits the inside diameter of the guide channel defined by the third guide sleeve. In this manner, the guide sleeve acts to guide and stabilize the third drill bit such that the third hole is substantially in the desired position and orientation of the implant. Although the drill bits utilized in actions 460-480 can be cannulated drill bits, because a guide pin is not used to guide and stabilize the drill bits, non-cannulated drill bits can be used.

The general actions associated with actions 460-480 can be repeated, but with guide sleeves having incrementally larger guide channels and incrementally larger drill bits, until the hole in the bone tissue reaches a desired diameter for implanting the dental implant. After the implant hole reaches the desired diameter, the guide splint is removed 485 from the patient's mouth.

With the guide pin removed from the patient's mouth in action 530 or the guide splint removed from the patient's mouth in action 485, a dental implant can be positioned within the resultant hole formed in the bone tissue and secured 490 therein using any of various dental implantation techniques known in the art, such as cementation or other bonding techniques.

The cannulated drill bit system and associated method described herein have certain advantages over non-cannulated drill bit systems and methods. For example, in some embodiments, a practitioner using a non-cannulated drill bit method, e.g., using sleeves in a splint to guide a drill bit as it drills a hole in the bone, may have difficultly viewing the bone during drilling. More specifically, the guide sleeves may block the practitioner's view of the bone as it is being cut. In contrast, because the drill bits of the cannulated drill bit system described herein fit over a guide pin, the practitioner is able to maintain a clear view of the bone being cut throughout the drilling procedure.

The schematic flow chart diagrams herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A dental implant drilling system for implanting a dental implant in bone tissue using an implant drill driver, comprising:
    a shank removably coupleable to the implant drill driver, the shank comprising a circumferentially enclosed internal passage having a non-round cross-sectional shape and a driver engagement portion comprising a first notched section, wherein when coupled to the implant drill driver, the shank is rotatable via operation of the implant drill driver;
    a drill guide pin comprising a bone penetrating end portion, a shank engagement end portion opposing the bone penetrating end portion, and an elongate shaft, the shank engagement portion comprising a second notched section having a non-round cross-sectional shape corresponding with the non-round cross-sectional shape of the internal passage of the shank, wherein the elongate shaft extends between the bone penetrating end portion and the second notched section, and wherein an intersection of the second notched section and elongate shaft comprises a stop that engages the shank to prevent axial movement of the drill guide pin relative to the shank; and
    a cannulated drill bit, wherein the drill guide pin is configured to receive thereabout the cannulated drill bit, and wherein the cannulated drill bit is removably coupleable to the implant drill driver;
    wherein the second notched section of the shank engagement portion is removably insertable within the internal passage of the shank, and wherein when the second notched section is inserted within the internal passage of the shank, engagement between the second notched section and the internal passage facilitates co-rotation of the shank and drill guide pin.

2. The dental implant drilling system of claim 1, wherein the non-round cross-sectional shape of the internal passage and the second notched section of the shank engagement portion is a generally D-shape.

3. The dental implant drilling system of claim 1, wherein the shank comprises a first driver coupling feature and the cannulated drill bit comprises a second driver coupling feature, and wherein the first and second driver coupling features are identical.

4. The dental implant drilling system of claim 1, wherein the second notched section of the shank engagement portion extends lengthwise along only a portion of the drill guide pin.

5. The dental implant drilling system of claim 1, wherein the internal passage extends axially through the shank from a first end of the shank to a second end of the shank.

6. The dental implant drilling system of claim 1, wherein a cross-sectional size of the second notched section of the shank engagement portion is smaller than a cross-sectional size of the internal passage of the shank.

7. The dental implant drilling system of claim 1, wherein the elongate shaft comprises a series of markings indicating a depth of the guide pin in bone tissue.

8. The dental implant drilling system of claim 1, wherein the second notched section has a cross-sectional area smaller than a cross-sectional area of the elongate shaft.

9. The dental implant drilling system of claim 1, wherein an outer surface of the elongate shaft is smooth.

10. The dental implant drilling system of claim 9, wherein the bone penetrating end portion comprises a pointed tip.

11. The dental implant drilling system of claim 1, wherein the guide pin is fluteless.

12. A method for drilling bone tissue, comprising:
   removably coupling a shank to a bone drill driver, the shank comprising an internal passage having circumferentially enclosed non-round cross-sectional shape extending an entire length of the shank and a driver engagement portion comprising a notched section;
   inserting a shank engagement portion of a guide pin into the internal passage of the shank until a stop formed in the guide pin contacts an end of the shank to prevent further axial movement of the guide pin along the internal passage, the shank engagement portion comprising a keyed-in section having a non-round cross-sectional shape matching the non-round cross-sectional shape of the internal passage of the shank;
   with the keyed-in section inserted within the internal passage of the shank, co-rotating the shank and the guide pin via actuation of the bone drill driver and engagement between the keyed-in section of the shank engagement portion of the guide pin and the internal passage of the shank;
   driving the guide pin into bone tissue;
   removing the shank engagement portion of the guide pin from the internal passage of the shank;
   decoupling the shank from the bone drill driver;
   removably coupling a cannulated drill bit to the bone drill driver;
   positioning the guide pin through the cannulated drill bit;
   rotating the cannulated drill bit via actuation of the bone drill driver; and
   driving the cannulated drill bit into bone tissue surrounding the guide pin.

13. A dental implant drilling system for implanting a dental implant in bone tissue using an implant drill driver, comprising:
   a shank removably coupleable to the implant drill driver, the shank comprising a circumferentially enclosed internal passage having a non-round cross-sectional shape and a driver engagement portion comprising a first notched section, wherein when coupled to the implant drill driver, the shank is rotatable via operation of the implant drill driver; and
   a drill guide pin comprising a bone penetrating end portion, a shank engagement end portion opposing the bone penetrating end portion, and an elongate shaft, the shank engagement portion comprising a second notched section having a non-round cross-sectional shape corresponding with the non-round cross-sectional shape of the internal passage of the shank, wherein the elongate shaft extends between the bone penetrating end portion and the second notched section, wherein an intersection of the second notched section and elongate shaft comprises a stop that engages the shank to prevent axial movement of the drill guide pin relative to the shank, and wherein the guide pin is fluteless;
   wherein the second notched section of the shank engagement portion is removably insertable within the internal passage of the shank, and wherein when the second notched section is inserted within the internal passage of the shank, engagement between the second notched section and the internal passage facilitates co-rotation of the shank and drill guide pin.

* * * * *